United States Patent [19]
Cerami et al.

[11] Patent Number: 5,770,571
[45] Date of Patent: Jun. 23, 1998

[54] METHOD AND AGENTS FOR INHIBITING PROTEIN AGING

[75] Inventors: Anthony Cerami; Yousef Al-Abed; Richard J. Bucala, all of New York, N.Y.; Peter C. Ulrich, Old Tappan, N.J.

[73] Assignee: The Picower Institute for Medical Research, Manhasset, N.Y.

[21] Appl. No.: 746,742

[22] Filed: Nov. 15, 1996

Related U.S. Application Data

[60] Provisional application No. 60/006,752 Nov. 15, 1995.
[51] Int. Cl.$^6$ ............................ A61K 38/00; C08J 89/06; C07K 13/00; A21D 4/00
[52] U.S. Cl. ................................. 514/12; 514/2; 524/12; 424/130.1; 530/300; 530/350; 426/133; 426/321
[58] Field of Search ............................ 524/21; 424/130.1; 514/2, 12; 530/300, 350; 426/133, 321

[56] References Cited

U.S. PATENT DOCUMENTS 4,665,192  5/1987  Cerami et al. .

OTHER PUBLICATIONS

Hayase et al., J. Biol. Chem., 263, pp. 3758–3764 (1989).
Sell et al., "Structure Elucidation of a Senescence Cross–link from Human Extracellular Matrix", J. Biol. Chem., 264, pp. 21597–21602 (1989).

*Primary Examiner*—W. Gary Jones
*Assistant Examiner*—Dianne Rees
*Attorney, Agent, or Firm*—Klauber & Jackson

[57] ABSTRACT

The present invention relates to compositions and methods for inhibiting the aging of amino-containing amino acid, peptides, proteins and biomolecules. Accordingly, a composition is disclosed which comprises an agent or compound capable of reacting with the glycosyl-amino moiety of the early glycosylation product (also known as the Amadori product or the Heyns product) formed by the reaction of glucose, or other reactive sugars, with an amino-containing peptide, protein or biomolecule, thus stabilizing this early glycosylation product, and preventing its further reaction to form open-chain, carbonyl-containing advanced glycosylation end products. Suitable agents may contain a reactive aldehyde group. A preferred agent is acetaldehyde. The method comprises contacting the target biomolecule with the composition. Both industrial and therapeutic applications for the invention are envisioned, as food spoilage and animal protein aging can be treated.

4 Claims, 11 Drawing Sheets

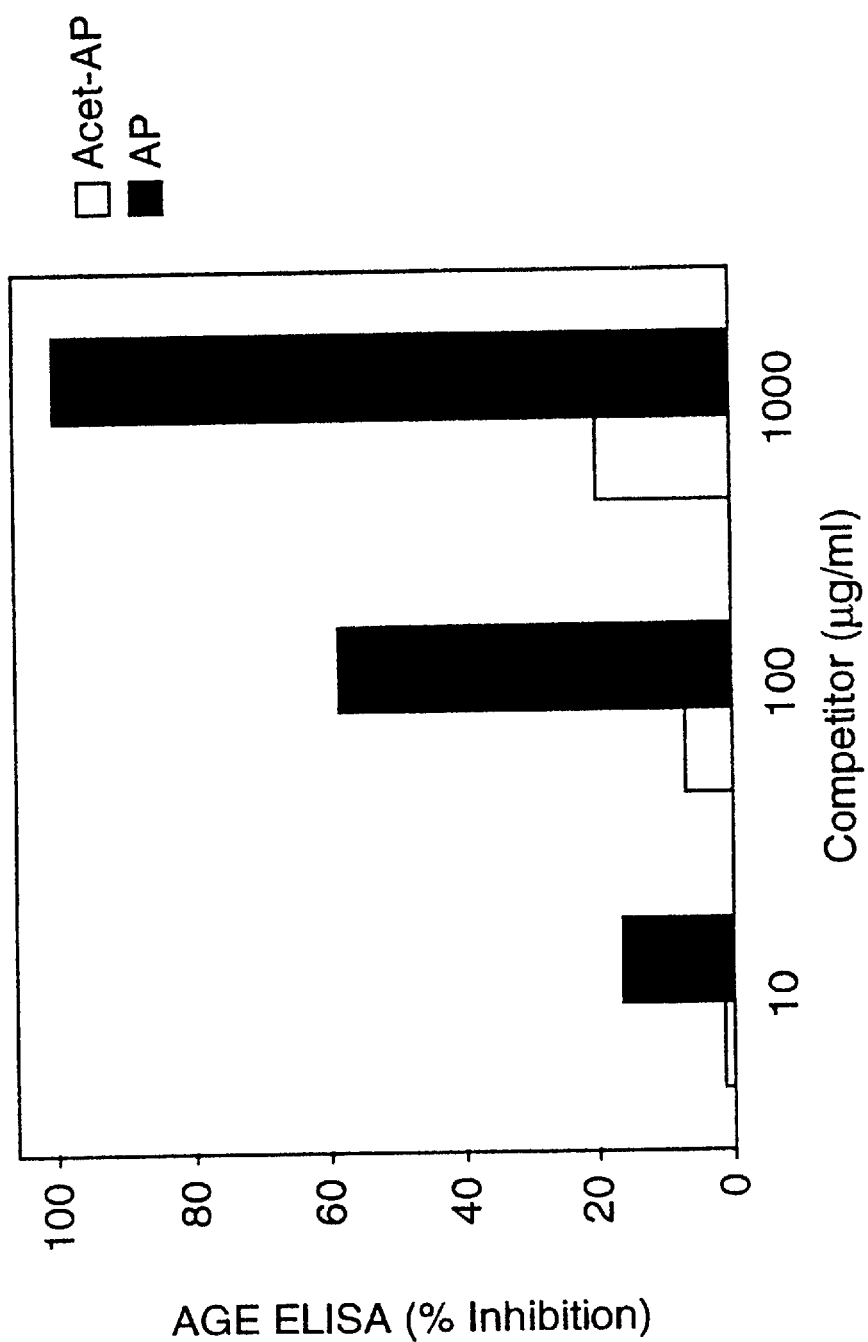

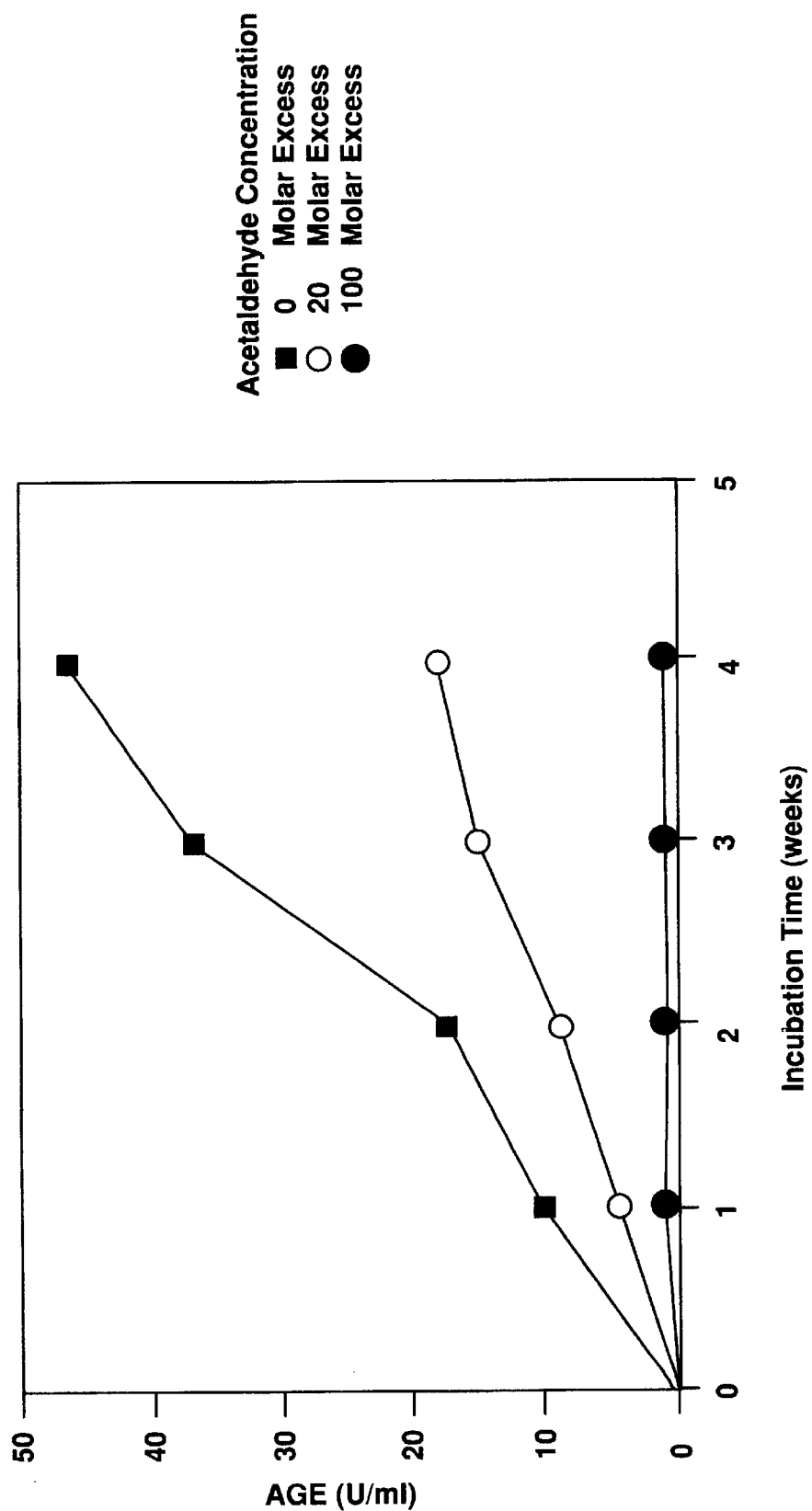

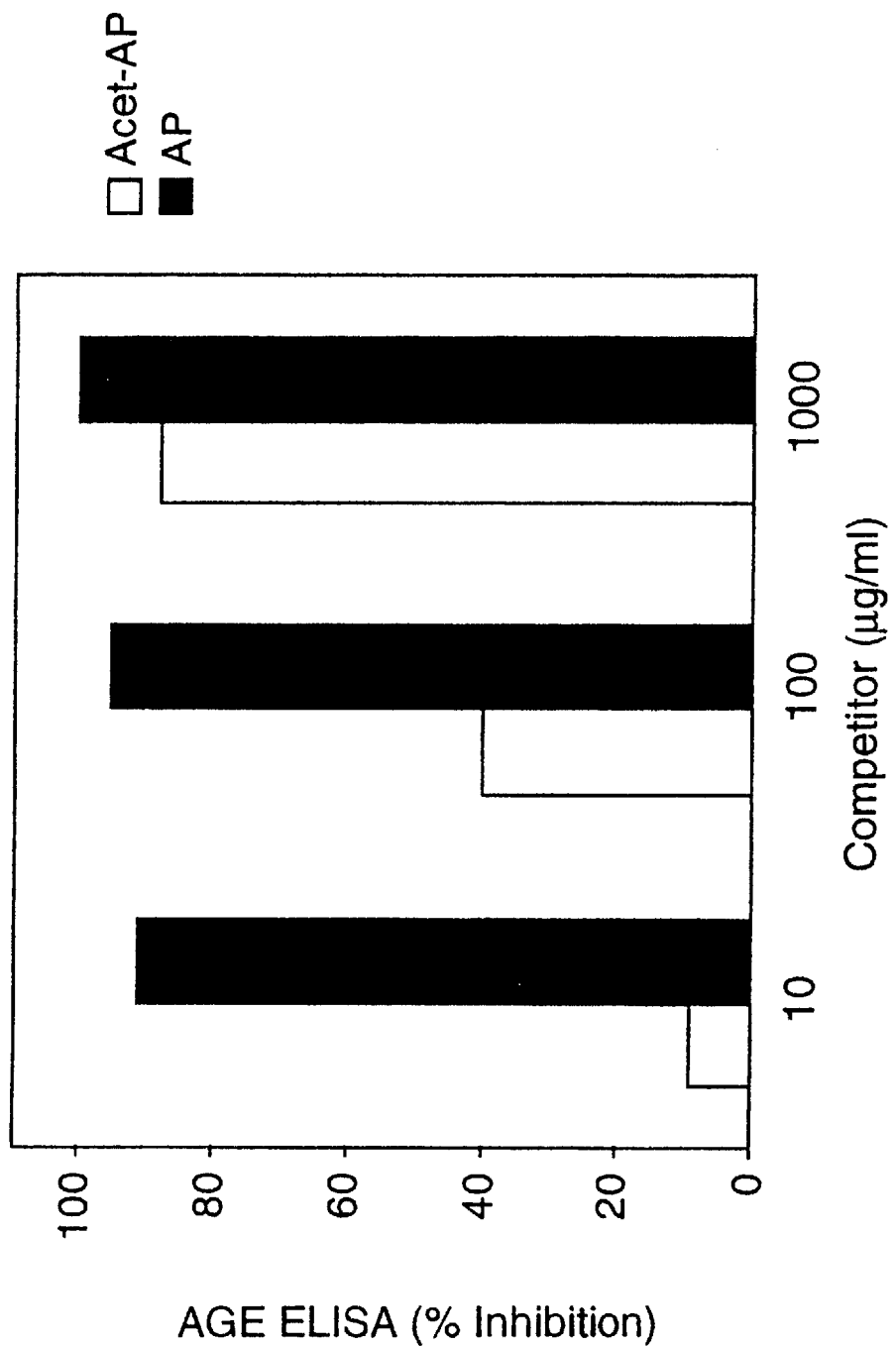

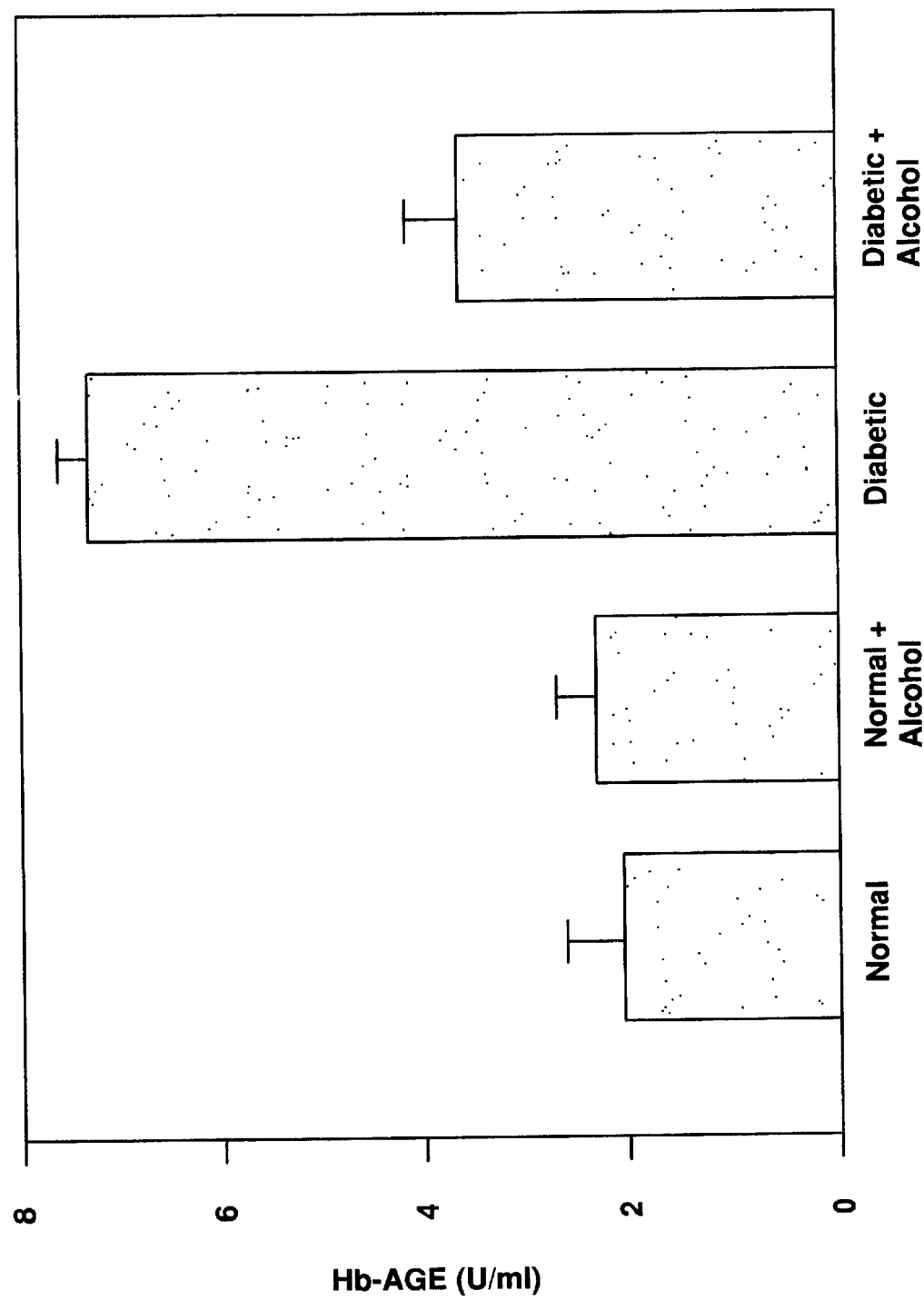

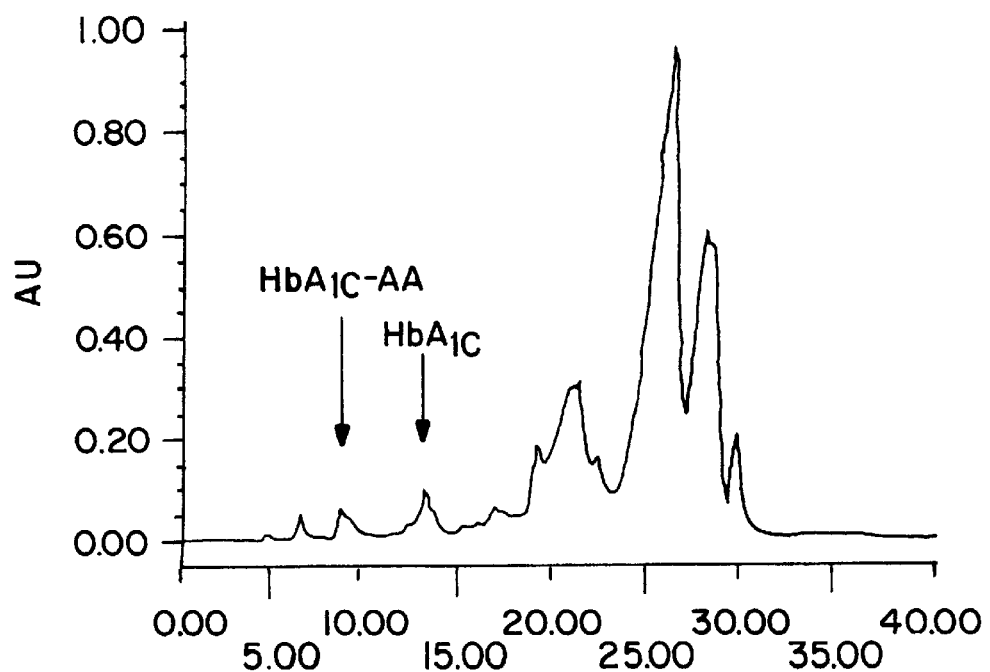
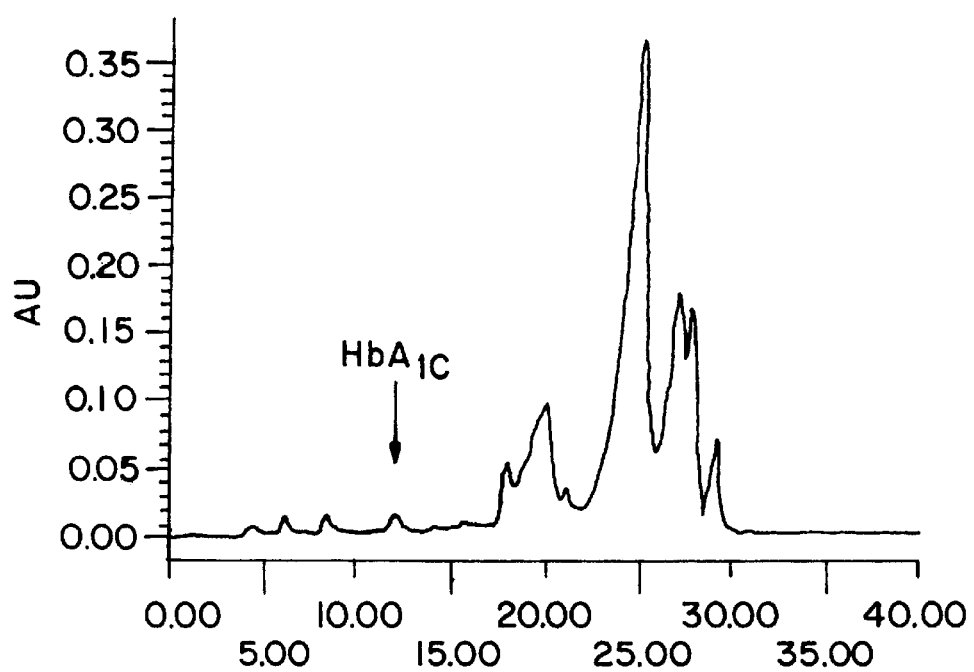

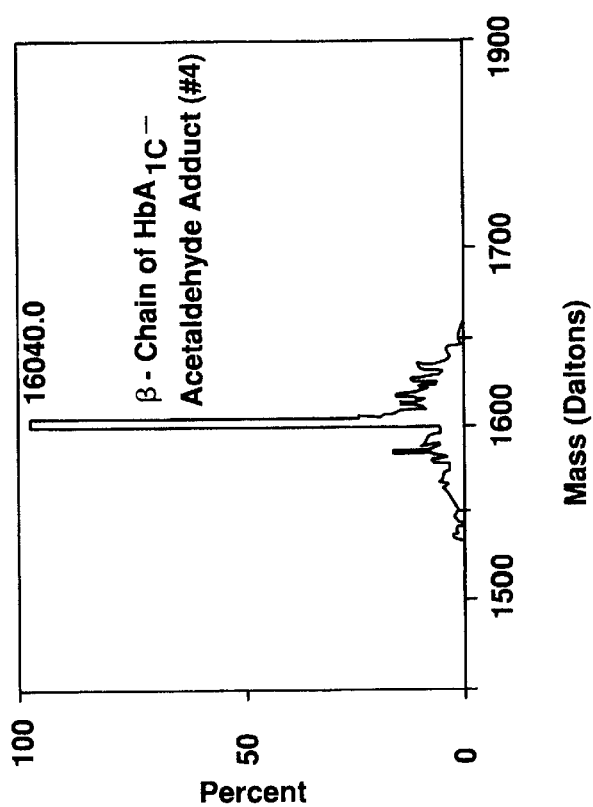

METHOD AND AGENTS FOR INHIBITING PROTEIN AGING

This Application claims priority from United States Provisional Application 60/006,752, filed Nov. 15, 1995.

This invention was made with partial assistance from a grant, DK19655 "Biochemical Basis of the Complications of Diabetes," from the National Institute of Diabetes and Digestive and Kidney Diseases of the National Institutes of Health.

BACKGROUND OF THE INVENTION

The present invention relates generally to the aging of proteins and other biomolecules resulting from reaction of glucose, and particularly to the non-enzymatic glycation or glycosylation of proteins and other susceptible amine-presenting molecules and subsequent reactions leading to advanced glycosylation end products, and to methods and agents for their inhibition.

The reaction between glucose and proteins has been known for many years. Its earliest manifestation was in the appearance of brown pigments during the cooking of food, which was identified by Maillard in 1912, who observed that glucose or other reducing sugars react with amino-containing compounds, including amino acids and peptides, to form adducts that undergo a series of dehydrations and rearrangements to form stable brown pigments.

In the years that followed the initial discovery by Maillard, food chemists studied this reaction in detail and determined that stored and heat-treated foods undergo non-enzymatic browning as a result of the reaction between glucose and the polypeptide chain, and that the proteins are resultingly crosslinked and correspondingly exhibit decreased bioavailability. At this point, it was determined that the pigments responsible for the development of the brown color that develops as a result of protein glycosylation possessed characteristic spectra and fluorescent properties.

The reaction between reducing sugars and food constituents discussed above was found in recent years to have its parallel in vivo. Thus, the non-enzymatic reaction between aldehyde sugars such as glucose, galactose and arabinose and the free amino groups on proteins to form a stable amino, 1-deoxy ketosyl adduct, is known as the Amadori product. In the case of ketone sugars such as fructose, this non-enzymatic reaction product is known as the Heyns product, with reactivities parallel to that of an Amadori product. This reaction has been shown to occur with hemoglobin, wherein a rearrangement of the amino terminus of the β-chain of hemoglobin, following an initial reaction with glucose, forms the modified hemoglobin known as hemoglobin $A_{1c}$. Similar reactions have also been found to occur with a variety of other peptides, proteins, both soluble and structural, and biomolecules, such as lens crystallins, collagen nerve proteins, and low density lipoproteins, DNA and aminophospholipids.

As a result of the recent interest in this area, the first few stages of the Maillard reaction, and a relatively limited number of associated initial adducts and products, have become well-known. As subsequent reactions (including various dehydrations, oxidations, eliminations, condensations, cleavages, and other chemical changes) occur, however, a bewildering array of "early" and "late" glycation adducts and reactants is generated, and these are less well understood in molecular detail. As a group, the more advanced glycation adducts can be described as a class of yellow-brown, fluorescent pigments with intra- and inter-molecular crosslinking activity, wherein specific glycation entities are thought to occur at low abundance within the widely divergent pool of advanced glycation end products (or AGEs). Despite significant work over the last twenty years or so, the molecular structures of only a few of these later glycation adducts and products have been determined, and the contribution of identified, in vivo-formed advanced glycation structures to specific biological processes remains poorly understood.

In U.S. Pat. No. 4,665,192 the fluorescent chromophore 2-(2-furoyl)-4(5)-2(furanyl)-1H-imidazole was isolated and identified from certain browned polypeptides such as bovine serum albumin and poly-L-lysine. This chromophore made possible the identification of the advanced glycosylation end products and assisted additional investigations seeking to clarify the protein aging process and to identify the specific chemistry involved in order to develop methods and agents for its inhibition.

More recently, other advanced glycation products have been identified, such as Farmar et al., U.S. Ser. No. 097,856, filed Sep. 17, 1987; pyrraline (Hayase et al., "Aging of Proteins: Immunological Detection of a Glucose-derived Pyrrole Formed during Maillard Reaction in Vivo", *J. Biol. Chem.*, 263, pp. 3758–3764 (1989)); and pentosidine (Sell et al., "Structure Elucidation of a Senescence Cross-link from Human Extracellular Matrix", *J. Biol. Chem.*, 264, 15 pp. 21597–21602 (1989)).

A large body of evidence has been assembled to show that Maillard products as a whole underlie a wide variety of both normal and pathogenic activities and responses that occur as advanced glycation end products (or AGEs) accumulate in vivo. Such activity may be direct, as a consequence of the chemical reactivity of glycation products and adducts, or indirect, mediated by the cellular recognition of glycation adducts and products via AGE-specific binding proteins or receptors. An appreciation for the pathogenic potential of AGEs has suggested that interference with, or inhibition of, advanced glycation chemistry could be of enormous therapeutic benefit. The agent pimagedine (aminoguanidine), and other related compounds, have been found to be useful glycation inhibitors. This compound, and others like it, has been theorized to react with the carbonyl moiety of the early glycosylation product of a target protein formed subsequent to the initial non-enzymatic reaction with glucose or another reducing sugar, and thereby prevent further reaction to form open-carbonyl-containing advanced glycosylation end products.

Although pimagedine has shown a great therapeutic potential, there exist a need to discover and develop alternative glycation inhibitors, active, for instance, at different stages of the Maillard reaction and/or against a different spectrum of glycation intermediates and AGEs. Such alternates would provide additional treatment modalities against the deleterious sequelae of AGE accumulation in vitro and in vivo. The present invention is thus directed toward inhibition of the Maillard reaction, and is shown to operate through a mechanism not exploited previously in this regard.

Recently, it has been discovered that other naturally-occurring reducing sugars, including fructose, ribose and galactose, participate in non-enzymatic glycation and cross-linking. Because the methods and agents of the present invention block non-enzymatic crosslinking mediated by any such reactive sugars, they are expected to prevent fructose-mediated crosslinking as well. Cross-linking caused by other reactive sugars present in vivo or in foodstuffs, including ribose and galactose, would also be prevented by the methods and compositions of the present invention.

SUMMARY OF THE INVENTION

In accordance with the present invention, an improved method and associated agents are disclosed for the inhibition of the aging of amino-containing amino acids, peptides, proteins and biomolecules. In particular, agents for inhibiting protein aging due to the formation of advanced glycosylation end products may be selected from those materials capable of reacting with the glycosyl-amino moiety of the early glycosylation product (also known as the Amadori product or the Heyns product) formed by the reaction of glucose, or other reactive sugars, with an amino-containing peptide, protein, or biomolecule, thus stabilizing this early glycosylation product, and preventing its further reaction to form undesired open-chain, carbonyl-containing advanced glycosylation end products. Thus, for example, compounds or compositions having an active aldehyde substituent are suitable, and especially, compounds such as acetaldehyde. The molecular basis of action of these agents appears to involve the reaction with the early glycosylation product formed between glucose, or other reactive sugars, and an amino-containing peptide, protein, or biomolecule whereby the resulting tripartite reaction product is stable, precludes rearrangement of the early glycation product into an open-chain, carbonyl-containing configuration, and thus does not support further reactions that would continue the advanced glycation process. Irrespective of their underlying mechanism of action, these agents prevent the formation of advanced glycosylation end products, and associated molecular changes, such as crosslinks.

The present invention also relates to a method for inhibiting aging of amino-containing peptides, proteins or biomoleules by contacting the initially glycosylated protein at the stage of the early glycosylation product with a quantity of one or more of the agents of the present invention. In the several instances where the present method has industrial application, one or more of the agents may be applied to the peptides, proteins or biomolecules in question, either by introduction into a mixture of the same in the instance of a protein extract, or by application or introduction into foodstuffs containing the protein or proteins, all to prevent premature aging and spoilage of the particular foodstuffs and other comestibles. Other industrial amine-containing compounds and products, including, for instance, various drugs, various nutritional ingredients for parenteral administration and the like, may likewise benefit from treatment with agents of and/or by the methods of the present invention. The agents and methods of the present invention can be used to extend the useful storage life of such amino-group containing commercial products, by inhibiting the formulation of AGEs on said amino groups during storage of said product.

In the instance where the present method has therapeutic application, the animal host intended for treatment may have administered to it a quantity of one or more of the agents, in a suitable pharmaceutical form. Administration may be accomplished by known techniques, such as oral, topical and parenteral techniques such as intradermal, subcutaneous, intravenous, or intraperitoneal injection, as well as by other conventional means such as inhaled aerosols or nemubulized droplets. Administration of the agents may take place over an extended period of time at a dosage level of, for example, up to about 25 mg/kg.

The ability to inhibit the formation of advanced glycosylation end products carries with it significant implications in all applications where protein aging is a serious detriment. Thus, in the area of food technology, the retardation of food spoilage would confer an obvious economic and social benefit by making certain foods of marginal stability less perishable and therefore more available for consumers. Spoilage would be reduced, as would the expense of inspection, removal and replacement, and the extended availability of the foods could aid in stabilizing their price in the marketplace. Similarly, in other industrial applications where the perishability of proteins or other amino-containing biomolecules (e.g. lipids and DNA) or compounds (e.g. pharmaceutical compositions) is a problem, the admixture of the agents of the present invention in compositions containing such peptides, proteins, or biomolecules would facilitate the extended useful life of the same. Presently used food preservatives and discoloration preventatives such as sulfur dioxide, known to cause toxicity including allergy and asthma in animals, might be replaced with compounds such as those described herein.

The present method has particular therapeutic application as the Maillard process acutely affects several of the significant protein masses in the body, among them collagen, elastin, lens proteins, and the kidney glomerular basement membranes. These proteins deteriorate both with age (hence the application of the term "protein aging") and as one of the sequelae of diabetes melitus. Consequently, the ability to either retard or substantially inhibit the formation of advanced glycosylation end products carries the promise of favorably treating significant adverse effects of aging and of diabetes and, of course, improving the quality and perhaps duration of animal life, including for instance human life.

Accordingly, it is a principal object of the present invention to provide a method for inhibiting the extensive cross-linking of amino-containing peptides, proteins, biomolecules or other compounds that occurs as an ultimate consequence of the reaction of said peptides, proteins, biomolecules or other compounds with glucose or other reducing sugars, by inhibiting the corresponding formation of advanced glycosylation end products.

It is a further object of the present invention to provide a method as aforesaid which is characterized by a reaction with early glycosylation products.

It is a further object of the present invention to provide a method as aforesaid which prevents the rearrangement, cross-linking and other Maillard reactions of the said early glycosylation products to form the said advanced glycosylation end products.

It is a yet further object of the present invention to provide agents capable of participating in the reaction with the said early glycosylation products in the method as aforesaid.

It is a still further object of the present invention to provide therapeutic methods of treating the adverse consequences of aging, manifest, for instance, in the stiffening and embrittlement of animal protein and the browning and spoilage of foodstuffs and other comestibles.

Other objects and advantages will become apparent to those skilled in the art from a consideration of the ensuing description which proceeds with reference to the following illustrative drawings.

BRIEF DESCRIPTION OF THE DRAWINGS

FIG. 1A is a comparison of aliquots from incubations of CBZ-lysine-AP, with and without acetaldehyde, analyzed for immunoreactive AGE epitopes using an ELISA procedure based on a polyclonal anti-AGE antibody preparation.

FIG. 1B is a comparison graph of aliquots from incubations of CBZ-lysine-AP, with and without acetaldehyde, at various time points during the incubation period, analyzed for immunoreactive AGE epitopes using an ELISA procedure based on a polyclonal anti-AGE antibody preparation.

FIG. 2 is a comparison of aliquots from incubations of CBZ-lysine-AP, with and without acetaldehyde, analyzed for immunoreactive AGE epitopes using an ELISA procedure based on a monoclonal anti-AGE antibody preparation.

FIG. 6 is a bar graph comparing the Hb-AGE values determined from blood samples taken at 8 weeks after the initiation of the study.

FIG. 9A is the ESMS spectra of the β-chain of the $HbA_{1c}$-acetaldehyde adduct.

FIG. 9B is the ESMS spectra of $Hb_0$.

DETAILED DESCRIPTION OF THE INVENTION

Figure 3:
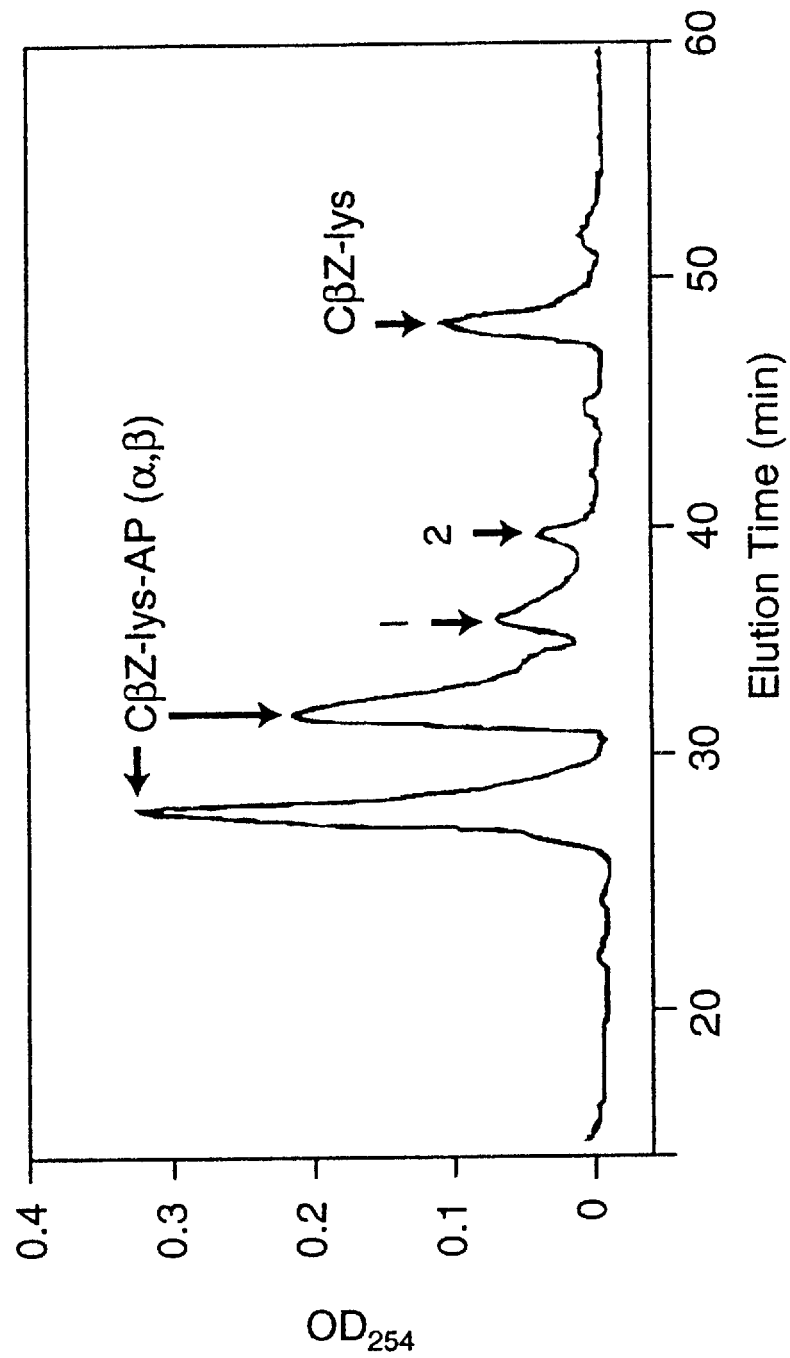
FIG. 3 is an HPLC analysis of the incubation mixture of CBZ-lysine-AP with acetaldehyde.

In accordance with the present invention, compositions and associated methods have been developed which inhibit the formation of advanced glycosylation end products in a number of amino-containing amino acids, peptides, proteins and biomolecules existing in both animals and plant material. In particular, the invention relates to compositions which may contain one or more agents for inhibiting aging due to the formation of advanced glycosylation end products, said agents selected from those materials capable of reacting with the glycosyl-amino moiety of the early glycosylation product (also known as the Amadori product or the Heyns product) formed by the reaction of glucose, or other reactive sugars, with a molecule bearing one or more amino groups, such as an amino acid, peptide, protein, other biomolecule or other organic compound, thus stabilizing said early glycosylation product, and preventing its further reaction to form open-chain, carbonyl-containing advanced glycosylation end products.

Reaction Scheme I, shown below, illustrates the first steps of the Maillard reaction, which describes the sequential spontaneous reactions of reducing sugars, with glucose being illustrated in the scheme, with amino-containing compounds, such as the ε-amino group of a lysine residue in a peptide or protein. The Maillard reaction thus begins with the non-enzymatic and readily reversible reaction between a sugar molecule (Ia or Ib) and an amino group of a peptide or protein (II) to form a Schiff base (IIa or IIb), which can then rearrange to form the Amadori product (IVa or IVb). Although illustrated by a series of open chain formulae (Ia, IIIa and IVa), it should be understood that the open form of each of these carbohydrate-protein adducts is in equilibrium with the corresponding closed ring form (Ib, IIIb and IVb), and this closed ring form generally predominates. More than 99% of the Amadori compound of formula IV is thus present in the closed ring configuration, which may involve either an α or β ring closure at carbon 2 (C2). The open chain Amadori product of formula IVa is free to dehydrate to generate the early glycation product 1-alkylamino-1,4-dideoxyglucosone (IX). These subsequent glycation products, especially the typical diketone type of formula IX, are believed to represent the class of substrates that can react with the advanced glycation inhibitor pimagedine (aminoguanidine).

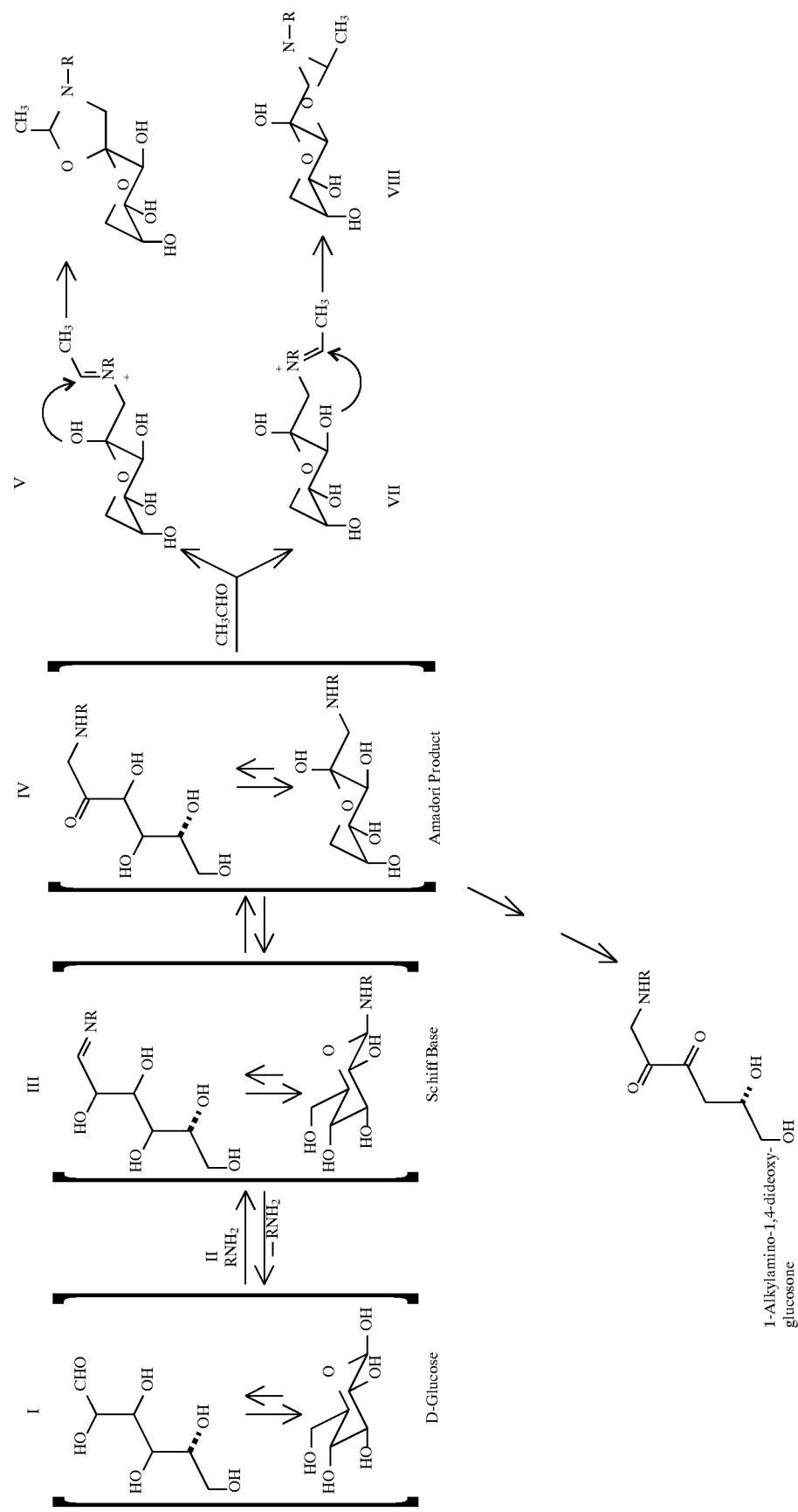

In Scheme I, the remaining portion of the amino acid, peptide, protein or other molecule bearing the amino substituent is denoted by R. Acetaldehyde is shown as the agent reactive with the glycosyl-amino moiety of the early glycosylation product of the amino acid, peptide, protein or other molecule bearing the amino substituent but other aldehydes may be substituted as descibed herein. Reactive sugars other than glucose will produce the corresponding Amadori product (e.g. the aldoses arabinose or galactose) or a Heyns product (e.g. the ketose fructose).

Applicants have now discovered that, as a distinct alternative approach to the inhibition the formation of advanced glycosylation end products (AGEs) by aminoguanidine-type inhibitory agents which target reactive carbonyls to inhibit more advanced stages of the Maillard reaction, a novel class of inhibitors can be utilized at an earlier stage, the typical Amadori product of Formula IV. Specifically, the glycosyl-aminoalkyl moiety of the Amadori product of formula IV can be reacted with an agent containing a reactive aldehyde group (illustrated in Scheme I by acetaldehyde, a representative species of the present invention) to form the unisolated intermediates of formulae V or VII, which then rearrange to form the stabilized closed configuration adducts of formulae VI and VIII, respectively. These adducts of formulae VI and VIII are stable, closed ring structures which are blocked from participating in subsequent steps of the advanced glycation (or Maillard) reaction, thus inhibiting the browning and crosslinking associated with AGE formation.

The thus-formed adducts of formulae VI and VIII thus eliminate the possibility of further typical glycation reactions, and the detrimental consequences which flow therefrom and result in the development in vivo of conditions such as skin wrinkling, certain kidney diseases, atherosclerosis, osteoarthritis and the like. Similarly, amino-containing plant, animal and chemical materials that undergo non-enzymatic browning deteriorate and, in the case of foodstuffs or other comestibles, become spoiled or toughened and consequently, unpalatable or inedible. Thus, the reaction of the compounds of the present invention with a susceptible early stage glyco-amino group is believed to inhibit the late stage Maillard effects and intervene in the deleterious changes described above.

The rationale of the invention is to use agents which covalently lock early stage glycation adducts into unreactive tripartite products, thus blocking later post-glycosylation steps, e.g., the formation of fluorescent chromophores whose presence is associated with, and leads to, the adverse sequelae of diabetes and aging. An ideal agent would prevent the formation of advanced AGE chromophores and associated or independent glycation cross-links, which can interconnect protein domains intra- or intermolecularly and covalently trap soluble proteins onto matrix proteins, as occurs in arteries and in the kidney. This crosslinking may itself be undesirable, as may be the cellular responses to crosslinked or other AGE-modified tissue and circulating components.

The present invention does not attempt to prevent the most initial steps of protein glycosylation, as the reaction of glucose with protein amino groups is very rapidly reversible and shortlived. Instead, the agents of the present invention are directed to the Amadori and Heyns rearrangement products which are less rapidly reversible and accumulate to a significant degree. Covalent interaction to form the addition products of the present invention serves to prevent or inhibit the long-term, late glycosylation steps that lead to the formation of advanced glycosylation end products that are a direct cause of the pathology associated with aging and diabetes.

It is the amine group of a protein or other biomolecule which initially reacts with the glucose, or another reactive sugar, to form an Amadori or Heyns rearrangement product, which is believed to react with the compounds of the present invention to form a terminal tripartite addition product.

Accordingly, the compositions useful in the present invention comprise or contain one or more agents for inhibiting protein aging due to the formation of advanced glycosylation end products, and may be selected from those materials capable of reacting with the early glycosylation product (also known as the Amadori product or the Heyns product) formed from the reaction of glucose, or other reactive sugars, with a free amino group on a second molecule such as a protein, thus stabilizing this early glycosylation product, and preventing its further reaction to form open-carbonyl-containing advanced glycosylation end products.

Suitable agents include compounds having a reactive aldehyde group which are represented by the general formula

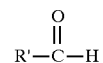

wherein R' is an alkyl group of 1–12 carbons, an alkenyl group of 1–20 carbon atoms containing 1–4 degrees of unsaturation, and alkynyl group of 1–20 carbon atoms containing one or more triple bonds, an aryl or a heteroaryl group, each of which can optionally be substituted by one or more halogen or hydroxyl groups. Also utilizable in the present invention are compounds which contain group which is metabolically transformed into an reactive aldehyde group.

For example, the agent may comprise an aldehyde compound such as acetaldehyde, or an alcohol, such as ethanol, which is metabolized in vivo to a corresponding aldehyde, in this case, acetaldehyde. Reaction of the agents of the present invention with the glycosyl-amino moiety, e.g. of a glycation-modified protein, would lock this nitrogen into a stable ring system and thus prevent an early glycation product from progressing to form undesired products, such as crosslinks with other groups.

Thus, the agents of the present invention have been identified and tested on the basis of their ability to react with the glycosyl-amino moiety of the Amadori or Heyns rearrangement glycosylation product to form a highly stable class of adducts. These agents contain a reactive aldehyde group, or a functional group which is metabolized in vivo to a reactive aldehyde group.

A representative agent of the present invention comprises acetaldehyde. This compound is known to have low toxicity in animals. According to the Handbook of Toxicology, Vol. 1, acetaldehyde base has a $LD_{50}$ when administered orally of 1.9 g/kg in rats. It can thus be utilized to react with the glycosyl-amino moiety of the Amadori products of formula IV to form the stable, non-reactive adducts of formula VI and VIII.

Other agents which have utility in the compositions and methods of the present invention are compounds which contain reactive aldehyde groups such as:

Phenylacetaldehyde;
2-Phenylpropionaldehyde;
Cinnamaldehyde;

α-Methylcinnamaldehyde;
α-Hexylcinnamaldehyde;
o-Methoxycinnamaldehyde;
Benzaldehyde;
o-Anisaldehyde;
Salicylaldehyde;
4-Ethylbenzaldehyde;
Cuminaldehyde;
p-Anisaldehyde;
4-Hydroxybenzaldehyde;
p-Ethoxybenzaldehyde;
2,4-Dimethylbenzaldehyde;
β-Cyclocitral;
3,4-Dihydroxybenzaldehyde;
Veratraldehyde;
Piperonal;
Vanillin;
Ethyl Vanillin;
Acetaldehyde;
Propionaldehyde;
Isobutyraldehyde;
Butyraldehyde;
2-Methybutyraldehyde;
2-Ethybutryaldehyde;
3-Methybutyraldehyde;
Valeraldehyde;
2-Methylpentenal;
Hexanal;
Heptanal;
Octanal;
Nonanal;
Decanal;
Laurio aldehyde;
3-(Methylthio)butanal;
Pyruvaldehyde;
trans-2-Pentenal;
trans-2-Methyl-2-butenal;
3-Methyl-2-butenal;
trans-2-Hexenal;
trans-2-Heptenal;
cis-4-Heptenal;
2,6-Dimethyl-5-heptenal;
trans-2-Octenal;
2-Isopropyl-5-methyl-2-hexenal;
2-Nonenal;
cis-6-Nonenal;
2-Decenal;
10-Undecenal;
trans,trans-2,4-Octadienal;
trans,trans-2,4-Nonadienal;
trans-2,cis-6-Nonadienal;
trans,trans-2,6-Nonadienal;
2,4-Hexadienal;
trans,trans-2,4-Decadienal;
(S)-(-)-Perillaldehyde; and
(1R)-(-)-Myrtenal.

The use of such compounds would result in compounds of formula VI and VIII wherein the methyl group of acetaldehyde, as illustrated, is replaced by the non-reactive portion of a compound containing the active aldehyde group.

As herein noted, also equivalent to the agents of the present invention containing a reactive aldehyde group are those agents containing a functional group which is metabolically converted in vivo to a reactive aldehyde group. For instance, ethyl alcohol or ethanol, when metabolized by the body, produces acetaldehyde as the principal product. Ethyl alcohol can thus be used as a therapeutic agent for in vivo applications of the present invention.

The measurement of the adducts of formula VI and VIII present in an animal or other protein-containing material can provide an indication of the amount of reactive aldehyde to which the animal or other protein-containing material has been exposed, thus leading to both diagnostic and monitoring utilities for this invention.

For instance, since ethyl alcohol produces acetaldehyde in vivo, the measurement of the corresponding adducts of formula VI and VIII formed from acetaldehyde can likewise be used to assess or monitor the ingestion of ethyl alcohol over periods of time. The present invention can thus be utilized to make an assessment of the alcohol ingestion by a patient over a period of time, since it would be expected that these adducts of formula VI and VIII will be stable and accumulate over time, and be identifiable in the patient's sera or other body fluids. The present invention thus finds utility in the area of screening for individuals who have, over a period of time, ingested ethyl alcohol, thus accumulating detectable amounts of the adducts of formula VI and/or VIII as a result of alcohol intake, and serving as a convenient marker of extended alchohol use or abuse. Similarly, the present invention finds utility in monitoring individuals for exposure to environmental, inhaled or ingested aldehydes, such as formaldehyde, and finds further utility in the preparation of dosimeter-type assays for the integrated exposure to reactive aldehydes.

The findings of the present invention can also be utilized to screen for additional agents which would have utility as agents for inhibiting advanced glycation. Thus, the measurement of the amount of the formation of the adducts of formula VI and/or VIII wherein the methyl group of the reacted acetaldyde, as illustrated, is replaced by the bulk of the test aqent bearing the reactive aldehyde of interest, would enable one to assess the usefulness of an agent as a potential inhibitor of the advanced glycation process.

The adducts of formula VI and VIII, or variants thereof comprising different aldehyde-bearing or amino-bearing reactants, may be used in standard fashion to prepare either polyclonal or monoclonal antibodies thereto for diagnostic purposes. Such antibodies are preparable by standard procedures, and thus enable the use of diagnostic assays for assessing and monitoring the effectiveness of therapeutic regimens where AGE inhibition has been initiated. Said immunological regents directed against generic and specific structures of the present invention are also useful to detect the degree of modification of Amadori or Heyns rearrangement products in a sample from a subject animal, including, for example, a human being, thereby to infer the recent history of alcohol consumption by said subject, by reference to a standard. Said polyclonal or monoclonal immunological reagents can optionally be included in a kit, with instructions, and, optionally, a standardized preparation of a tripartite compound of the present invention, to facilitate such determinations all as contemplated hereunder.

In the instance where the composition of the present invention is utilized for in vivo or therapeutic purposes, it may be noted that the compounds or agents used therein are biocompatible. Pharmaceutical compositions may be prepared with a pharmaceutically effective quantity of the agents or compounds of the present invention and may include a pharmaceutically acceptable carrier, selected from known materials utilized for this purpose. Such compositions may be prepared in a variety of forms, depending on the method of administration. For example, a liquid form would be utilized in the instance where administration is by intravenous or intraperitoneal injection, which liquid might be aerosolized for delivery by inhalation; while, if appropriate, tablets, capsules, etc., may be prepared for oral administration. For application to the skin, a lotion or ointment may be formulated with the agent in a suitable vehicle, perhaps including a carrier to aid in penetration into the skin. Other suitable forms for administration to other body tissues are also contemplated.

The present invention likewise relates to methods for inhibiting the formation of advanced glycosylation end products, which comprise contacting the target proteins with a composition of the present invention. In the instance where the target proteins are contained in foodstuffs or other comestibles, whether of plant or animal origin, these foodstuffs could have applied to them by various conventional means a composition containing the present agents. Similarly, amino-containing compounds such as drugs or ailimentary supplements that deteriorate or otherwise become spoiled over time by advanced glycation can be protected by treatment with an agent of the present invention that is biocompatibly non-toxic, and does not inactivate the desired characteristics of the compound in need of preservation. Protocols are provided for the identification of agents of the present invention useful in such contexts. Likewise, in the instance where therapeutic applications are intended, the animals to be treated would have administered to them a regular quantity of the pharmaceutical composition of the present invention. Administration could take place, for example, daily, and an effective quantity of the agent or compound of the present invention could range up to 25 mg/kg of body weight of the animal. A topical preparation may, for example, include up to 10% of the agent or composition in an ointment or lotion for application to the skin. Naturally, some variation in these amounts is possible, and the suggested amounts are provided in fulfillment of applicants' duty to disclose the best mode for the practice of the present invention.

As is apparent from a discussion of the environment of the present invention, the present methods and compositions hold the promise for arresting the aging of key molecules, whether in animal or plant material, or in chemical preparations, and whether in vivo or in vitro, and concomitantly conferring both economic and medical benefits as a result thereof. In the instance of in vitro use for preserving consumable materials, such as foodstuffs and other comestibles, from undersired deterioration, the administration of the present compositions holds the promise of retarding spoilage and thereby increasing shelf life and providing more convenience and greater availability to consumers. Replacement of currently-used preservatives, such as sulfur dioxide known to cause allergies and asthma in humans, with non-toxic, biocompatible compounds is a further advantage of the present invention.

The in vivo therapeutic implications of the present invention relate to the arrest of several of the pathogenic activities associated with the aging process which have, as indicated earlier, been identified in the aging of key tissue and circulating proteins by advanced glycosylation and crosslinking. Thus, body proteins, and particularly structural body proteins such as collagen, elastin, lens proteins, nerve proteins and kidney glomerular basement membranes would all benefit in their longevity and operation from the practice of the present invention. The present invention thus reduces the senescence caused by pathologies involving the entrapment of proteins by crosslinked target proteins, as exemplified, for instance, in retinopathy, cataracts, diabetic kidney disease, glomerulosclerosis, peripheral vascular disease, arteriosclerosis obliterans, peripheral neuropathy, stroke, hypertension, atherosclerosis, osteoarthritis, periarticular rigidity, loss of elasticity and wrinkling of skin, stiffening of joints, glomerulonephritis, etc. Likewise, all of these conditions are in evidence in patients afflicted with diabetes mellitus. Thus, the present therapeutic method is relevant to treatment of the noted conditions in patients either of advanced age or those suffering from one of the mentioned pathologies, particularly in association with hyperglycemia, which accelerates glycation-mediated senescence.

Protein crosslinking through advanced glycosylation product formation can decrease solubility of structural proteins such as collagen in vessel walls, and as well as trap serum proteins, such as lipoproteins to the collagen. Also, this may result in covalent trapping of extravasated plasma proteins and lipoproteins in subendothelial matrix, and reduction in susceptibility of both plasma and matrix proteins to physiological degradation by enzymes. For these reasons, the progressive occlusion of diabetic vessels induced by chronic hyperglycemia has been hypothesized to result in part from excessive formation of glucose-derived adducts and crosslinks. Such diabetic macrovascular changes and microvascular occlusion can be effectively prevented by chemical inhibition of advanced glycosylation product formation utilizing a composition and the methods of the present invention.

Taken together, these data strongly suggest that inhibition of the formation of advanced glycosylation end products (AGEs), by the teachings of the present invention, may prevent late as well as early structural lesions due to diabetes, as well as changes during aging caused by the formation of AGEs.

The present invention will be better understood from a consideration of the following illustrative examples, reviewing the selection and testing of certain of the agents of the present invention on both an in vitro and in vivo basis.

This invention may be embodied in other forms or carried out in other ways without departing from the spirit or essential characteristics thereof. The present disclosure is therefor to be considered as in all respects illustrative and not restrictive, the scope of the invention being indicated by the appended claims, and all changes which come within the meaning and range of equivalency are intended to be embraced therein.

Specifically, Applicants describe herein the covalent reaction of aldehyde agents with the Maillard Amadori product (or equivalent Heyns rearrangement product) (illustrative intermediates shown in Scheme I as V and VII) to consequently form a tripartite product, characterized by the presence of two adajacent ring systems, said rings being either spiro or fused bicyclic, wherein said tripartite product (e.g., VI and VIII) is stabilized against progression in the typical reactions of advanced glycation. Applicants show that this structural "locking" of the Amadori (or Heyns) structure in a closed configuration prevents the typical subsequent glycation reactions and inhibits the browning and crosslinking associated with AGE formation. The reaction mechanisms implied by the illustrative structural schemes are for explanatory purposes only, and should not be taken as a limitation on the scope of the present invention.

EXAMPLE 1

Structural confirmation of the Amadori-acetaldehyde adduct (AAA)

A simplified test reaction system was set up in vitro to provide evidence that aldehydes can react usefully with Amadori products, thus trapping these glycation intermediates in a closed and unreactive conformation and thereby largely prevent the process of advanced glycation. As shown in Scheme II below, a modified, lysine-based Amadori product was synthesized as a controlled starting material for advanced glycation reactions. This reagent, CBZ-lysine-AP, was prepared to be susceptible to advanced glycation at only one location (the $\alpha$-amino function of lysine was blocked by a carbobenzoxy group, leaving only the $\epsilon$-amino group available for glycation reactions). This model Amadori product was then incubated in the presence or absence of acetaldehyde, as a model agent of the present invention, both to test the effect of the supplied aldehyde agent on the progression of advanced glycation as well as to provide material for structural characterization to confirm the spontaneous formation of the expected Amadori-acetaldehyde adduct (AAA).

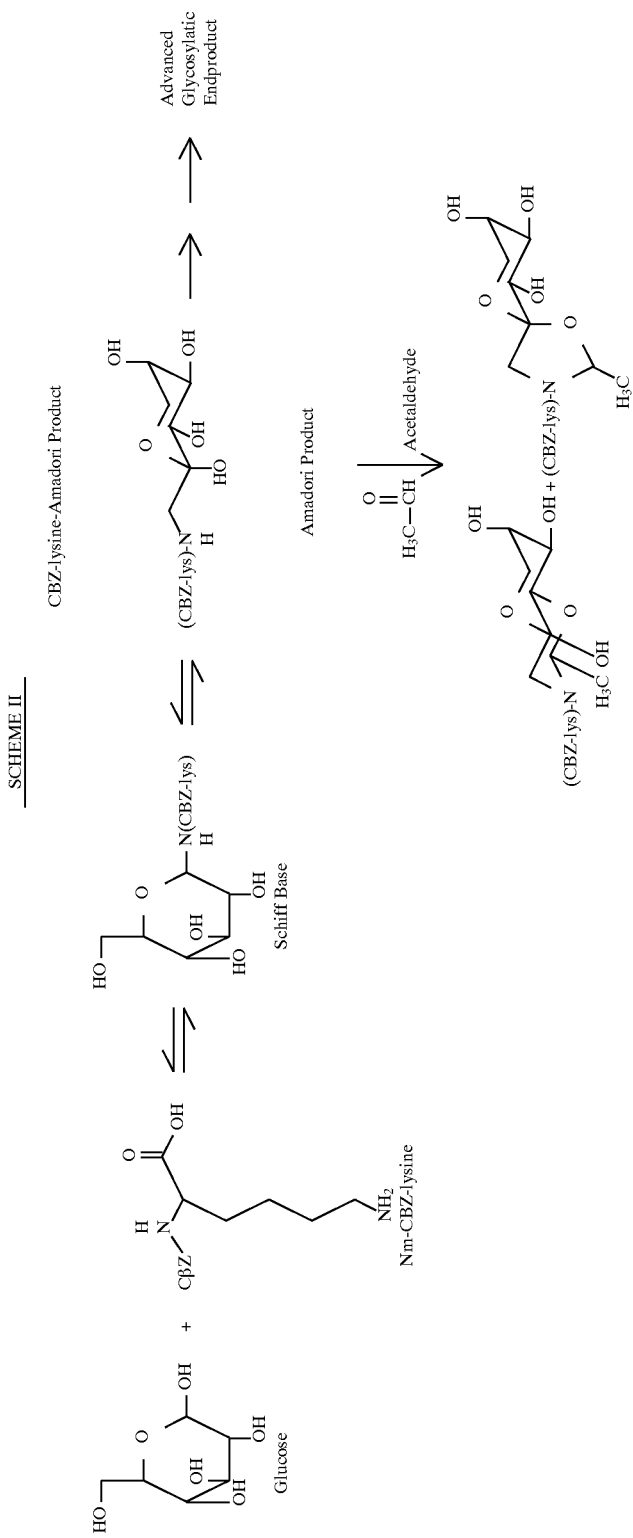

Preparation of N-(1-deoxy-D-fructos-1-yl)-$N^a$-carboxybenzoyloxy-lysine or CBZ-lysine-AP A suspension of 3.6 g (0.02 mol) of anhydrous D-glucose and 0.2 g of sodium bisulfite in 6 ml of methanol and 3 ml of glycerol was refluxed for 30 min, followed by addition of 7 mmol of $N^a$-carboxybenzoyloxy-lysine and 0.8 ml of acetic acid. This solution was refluxed until most of the starting material disappeared as evidenced by thin layer chromatography (TLC). TLC was performed on Silica Gel-60 manufacturer glass plates using the following irrigant (v/v): 4:1:1 n-butanol/acetic acid/water. Plates were sprayed with 0.2% ninhydrin in ethanol (for detection of lysine and sugar), followed by heating at 100° C. for about 5 minutes. The Amadori product was dissolved in methanol and poured into n-propanol with vigorous stirring. After standing for about 3 hours at room temperature, a yellowish oily material came out of solution. This upper layer was decanted and part of the oily material was subjected to preparative high performance liquid chromatography (HPLC) as follows. A Primesphere (Phenomenex, Torrance, Calif.) 5 m C18 HPLC column (250×21.2 mm;) was equilibrated in Buffer A (0.05% trifluroacetic acid [TFA]/95% $H_2O$), and the HPLC system was programmed to deliver a linearly increasing gradient of Buffer B (100% methanol) over 30 min (Buffer B=0% at 0 min; 100% at 30 min), at a flow rate of 8 ml/min. Column eluant was monitored with an ultraviolet detector set at 254 nm, and the new peak appearing at 33 min was isolated, lyophilized and analyzed by NMR and mass spectrometry, giving the following results, which are consistent with the structure shown in SCHEME II and labeled as CBZ-lysine-AP.

$^1$H-NMR (270 MHZ, $D_2O$): δ1.32 (m, 2H), 1.62 (m, 4H), 2.99 (t, 2H, J=7.6 Hz), 3.19 (s, 2H), 3.62–3.93 (m, 6H), 5.00 (d, 1H, J=12.6 Hz), 5.08 (d, 1H, J=12.5 Hz), 7.36 (m, 5H); $^{13}$C-NMR (67.5 MHZ, $D_2O$) δ22.2, 24.8, 31.2, 48.3, 52.8, 56.0, 64.0, 67.0, 69.0, 69.3, 69.6, 95.5, 127.7, 128.2, 128.4, 136.6, 158.0, 179.6.

Incubation of CBZ-lysine-AP with acetaldehyde

A solution of CBZ-lysine-AP (5 mg) in 2 ml of 0.2M phosphate buffer was subjected to prolonged incubation with 10 equivalents of acetaldehyde (about 25° C.). A parallel incubation was carried out at the same time, identical but for the absence of acetaldehyde. After five weeks, aliquots of each incubation mixture were analyzed by the following methods: visual inspection, AGE-ELISA (monoclonal and polyclonal antibody-based); absorption/fluorescence spectroscopy for excitation/emission maxima; HPLC; LC-MS (liquid chromatography-mass spectroscopy); and $^1$H-NMR (proton nuclear magnetic resonance spectroscopy).

Upon initial inspection, applicants noted that the incubation mixture which included acetaldehyde was clear and unpigmented while the solution of CBZ-lysine-AP incubated for five weeks in the absence of acetaldehyde was markedly yellow in color. Applicants took this as evidence that CBZ-lysine-AP went on, over time, to form more advanced (and pigmented) advanced glycation products but that the formation of such yellow pigmented AGEs was blocked by the formation of the expected Amadori-acetaldehyde adduct (AAA) when acetaldehyde was present in the incubation mixture. This conclusion was borne out by experimental measurement of AGE formation.

Aliquots from the two incubations were analyzed by two distinct competitive ELISA procedures, one based on polyclonal anti-AGE antibodies (FIGS. 1A and and the other on a monoclonal anti-AGE antibody (FIG. 2). Both procedures indicated that significantly more immunoreactive AGE epitopes had developed over time in the incubation of CBZ-lysine-AP without acetaldehyde than under identical incubation conditions but in the presence of acetaldehyde.

Fluorescence spectrometric analysis of these two incubation mixtures revealed the same wavelength of maximum excitation at 320 nm. The incubation mixture of CBZ-lysine-AP incubated with acetaldehyde showed maximal $δ_{em}$ at 388 nm while the parallel incubation mixture without acetaldehyde showed maximal $δ_{em}$ at 420 nm, the latter value consistent with the typical excitation/emission profile of AGEs.

Analysis of the incubation mixtures by HPLC (Primesphere 5μ C18 [250×21.2 mm] column; 0–50% Buffer B over 50 min at 7 ml/ min; UV monitoring at 254 nm) revealed two major peaks present in the incubation made with acetaldehyde that were not present in comparable HPLC analysis of the starting material (see FIG. 3, arrows marked 1 & 2). Eluant fractions corresponding to the central area of Peak 1 (identified in FIG. 3) were pooled, lyophilized and characterized by $^1$H-NMR and mass spectrometry.

Figure 4:
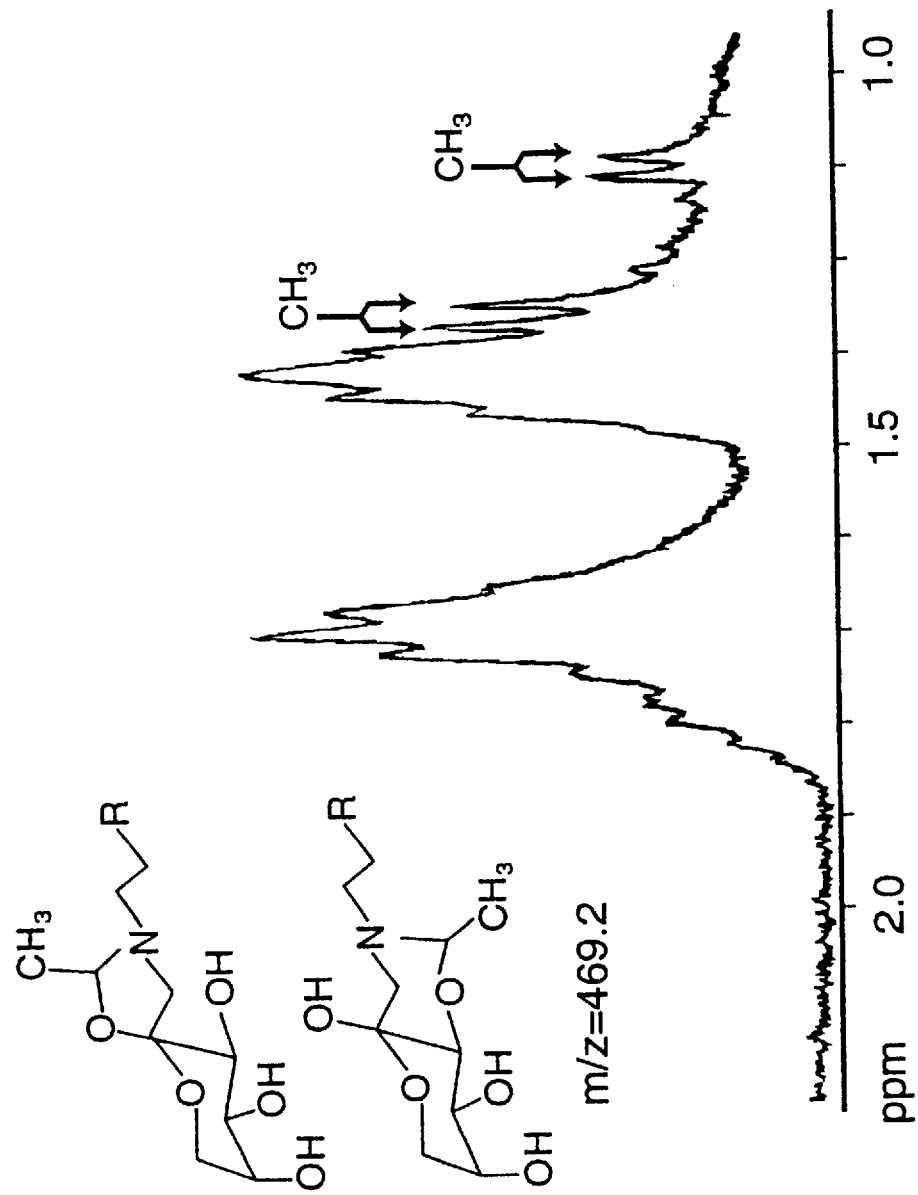
FIG. 4 is a partial upfield NMR spectrum of an HPLC-purified. fraction of the incubation mixture of CBZ-lysine-AP with acetaldehyde.
Figure 5:
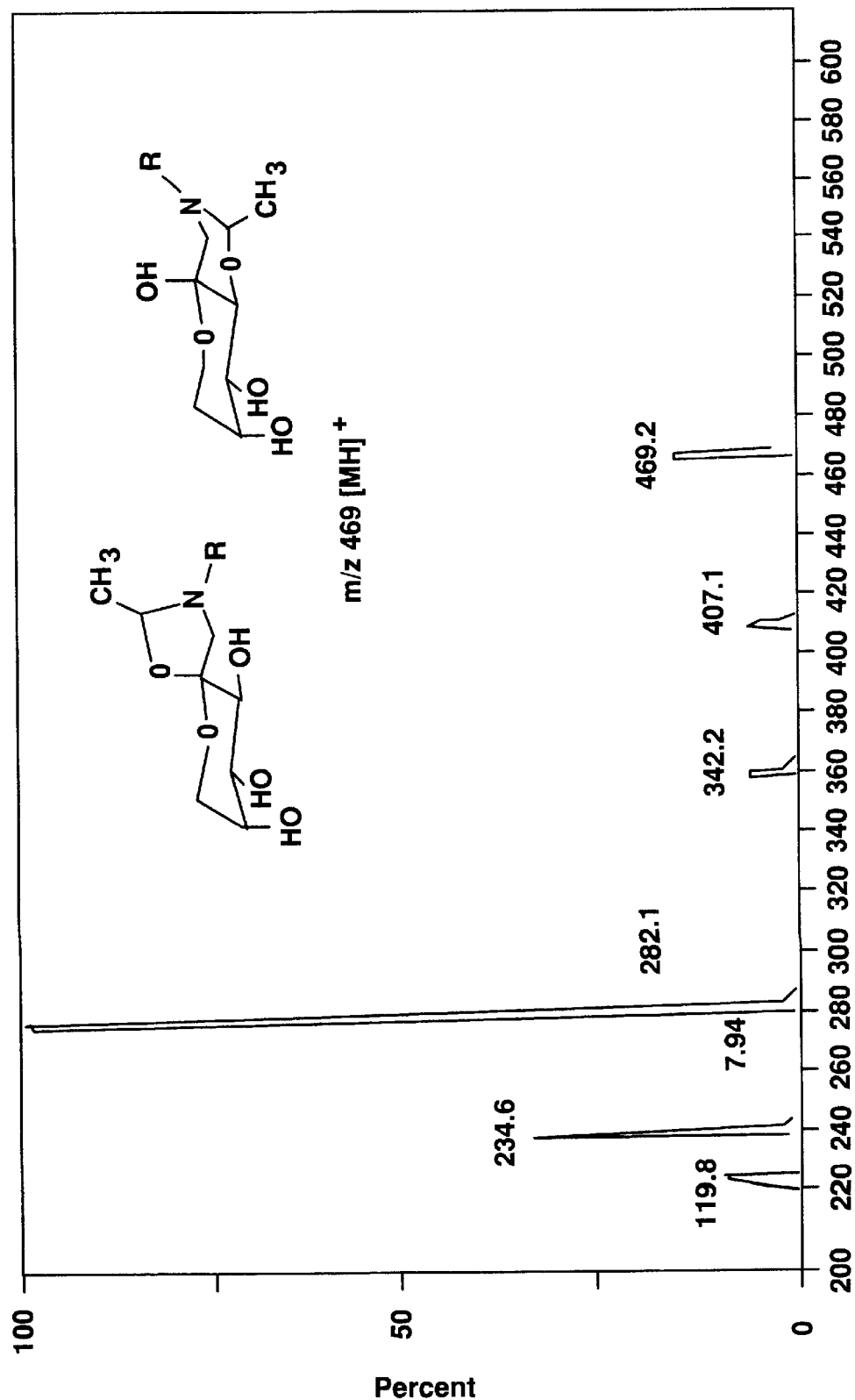
FIG. 5 is a mass spectrum of an HPLC-purified fraction of the incubation mixture of CBZ-lysine-AP with acetaldehyde.

The $^1$H-NMR spectrum of this fraction (FIG. 4) showed the appearance of two sets of methyl groups at δ1.1 and 1.27 ppm, each appearing as a doublet attributable to vicinal coupling with the methine proton (OC<u>H</u>N—). The presence of two such doublets is consistent with the presence of diastereomeric pairs of either the 5- or the 6-membered ring structures shown in Scheme II; or the formation of only a single sterioisomer of the 5-membered spirobicyclic AAA and a single sterioisomer of the 6-membered fused bicyclic AAA. The mass spectrum (FIG. 5) of this peak displayed a single molecular ion at m/z 469 (MH+), consistent with the identical molecular weights of the proposed structures whether they cyclize to form a 5- or 6-membered ring AAA. Both structures may exist as an equilibrium mixture. Other, minor products in the above reaction mixture could be assigned preliminary compositions on the basis of mass spectrometric data, indicating the integration of two acetaldehyde molecules with a single CBZ-lysine-AP molecule (MS m/z 513 [AP+$2CH_3CO$—$H_2O$]).

EXAMPLE 2

Applicants designed a second test system to define the activity of the aldehyde agents of the present invention as inhibitors of advanced glycation. In this in vitro system, a test protein is incubated with a reducing sugar, optionally with mild heating to accelerate the initial stages of the Maillard reaction. Aliquots of this pre-reacted protein sample are then incubated either in the presence or absence of an added aldehyde agent of the present invention, in order to measure the inhibitory effect of such added aldehyde agent on the glycation of a typical protein molecule under experimental browning conditions similar to the conditions of protein aging in vivo. In a working example, BSA (50 mg/ml) is incubated in 0.1M glucose at pH 7.5 for 48 hours at 37° C. in an aqueous buffer. During this abbreviated pre-incubation period, many of the lysine ε-amino groups of the protein condense with glucose to form initial Schiff-base (SB) adducts, which rearrange to generate the Amadori product (AP). After 48 hours, the BSA sample is dialyzed against buffer to remove unreacted glucose and other low molecular weight reactants. The protein sample then is divided into three portions (A, B, and C) to study the kinetics of protein aging and to measure the inhibition of this non-enzymatic glycation by typical model aldehyde agents of the present invention. Part A is not treated with added aldehyde, while parts B and C are incubated with an active aldehyde agent of the present invention, in this case acetaldehyde and 4-hydroxybenzalaldehyde, respectively. Each of the experimental preparations are incubated for five weeks at room temperature, and samples of are were collected every week and stored at −20° C. for later analysis. At the end of the incubation, the collected samples are assessed for AGE content by: (1) visual inspection for colored products; (2) fluorescence spectroscopy to determine excitation/emission profiles and wavelength maxima; and (3), AGE-ELISA (both monoclonal and polyclonal antibody-based). By each of these tests, significantly fewer AGEs are present in the incubations that included an added aldehyde agent of the present invention than in control incubations without the added aldehyde agent.

EXAMPLE 3

In vivo studies

When ethanol is consumed it is converted into acetaldehyde by the activity of constitutive and inducible alcohol dehydrogenase enzymes. Applicants considered that the elevation of acetaldehyde levels in vivo by chronic consumption of ethanol would be reflected in an inhibition of the normal accumulation of AGEs and AGE-modified proteins in the body. Because AGE levels in normal animals, including humans, is low and AGE accumulation progresses only slowly with aging, Applicants considered that an in vivo demonstration of the AGE-inhibiting activity of the metabolic products of ingested ethanol might conveniently be demonstrated in diabetic animals, which much more rapidly accumulate AGEs and show elevated circulating and tissue AGE levels as a consequence of their chronic hyperglycemia. Applicants predicted that, in a diabetic population, ethanol consumption would be clearly reflected in a diminishment of the hyperglycemia-dependent elevation in AGE levels, because consumed ethanol would be converted to acetaldehyde in vivo, and the consequent reaction of this acetaldehyde with Amadori products would lock these glycation intermediates into an unreactive closed configuration (i.e, AAA-type adducts), thus inhibiting progression of the Maillard reaction and lowering the accumulation of AGEs that would otherwise be expected to occur in conjunction with diabetes. Since hemoglobin is well-known to become spontaneously glycated, forming both hemoglobin $A_{1c}$ ($HbA_{1c}$; which is modified by an Amadori product), as well as hemoglobin-AGE (Hb-AGE; which is modified by advanced glycation end products), Applicants considered hemoglobin to represent a convenient substrate by which to measure the effects of alcohol consumption on in vivo AGE levels. Applicants also recognized that measurements of the glycation status of hemoglobin, or of other conveniently measured substrates for AGE formation, would provide a ready marker for the recent history of alcohol consumption by a subject.

To verify these related predictions in an animal model system, Applicants chose to induce diabetes and hyperglycemia in rats, which could then be fed an ethanol-supplemented diet. Later, blood samples could be tested for Hb-AGE levels relative to controls (not fed ethanol) as an index of alcohol consumption. Accordingly, male outbred Wistar rats (HSD:Wi), weighing between 150–175 g (approximately 6 weeks old) were group housed (three per cage) and provided standard laboratory rat chow and water ad libitum during an adaptation period of one week. Half of these rats were then treated with streptozotocin (65 mg/kg) to induce diabetes mellitus and hyperglycemia. Diabetes was confirmed a 1 week by measurement of blood glucose (440 +/− 38 mg/dl for the streptozotocin-treated group of rats). Diabetic streptozotocin-treated rats were paired by matching blood glucose levels. One rat from each pair was assigned to Group 1 and one to Group 2, so that blood glucose levels were matched between these two groups. Control rats (not treated with streptozotocin) were randomly assigned to Groups 3 and 4 (non-diabetic). All animals were then placed on one of two calorically matched liquid diets ad libitum (Bio-Serve Ethanol Diet or Bio-Serve Caloric Control Diet; Bio-Serve, Frenchtown, N.J.). Groups I and 3 received control diet, while Groups 2 and 4 received the ethanol-supplemented diet (36% of calories as ethanol). Pilot experiments revealed that diabetic rats in particular also required supplemental water under this protocol. In subsequent experiments, all animals were provided the control liquid diet rather than standard chow during the acclimation period, and groups scheduled to receive ethanol were switched to the ethanol-supplemented diet according to the protocol outlined. Blood samples were taken periodically from rats in all groups for determination of total hemoglobin, $HbA_{1c}$, Hb-AGE, and blood glucose levels.

Hb-AGE values were determined from blood samples taken two weeks after the experimental groups were switched to ethanol-supplemented diets. Table I below shows that Hb-AGE levels in diabetic rats fed a high ethanol diet were significantly lower than Hb-AGE levels in diabetic rats fed an isocaloric control diet without ethanol at the two-week point. FIG. 6 shows that Hb-AGE levels were significantly lower in diabetic rats fed a high alcohol diet than in diabetic rats fed the iocaloric, control diet (without alcohol) as determined from blood samples taken at approximately one month after the initiation of the diet protocol.

As predicted $HbA_{1c}$ levels did not differ between the two groups, indicating that alcohol treatment did not affect the formation of the Amadori product, the Hb-AGE precursor. Since the assay for $A_{1c}$ does not discriminate betwwen acetaldehyde-$A_{1c}$ and $A_{1c}$, this is to be expected. The $HbA_{1c}$ data also served to confirm that both experimental groups experienced the same degree of hyperglycemia.

By way of explanation, but without limitation, this result may reflect the covalent modification of hemoglobin-Amadori product intermediates by acetaldehyde arising by conversion from dietary ethanol. These acetaldehyde-reacted Amadori products will be locked in their closed conformation, and thus inhibited from progressing through the Maillard reaction to generate more advanced glycation products. Irrespective of the exact chemical mechanism, ethanol consumption will be reflected quantitatively and qualitatively in the modification of proteins by AGEs in vivo, and measurement of the type and/or degree of such alterations in the normal Maillard processes and products will reflect the recent history of alcohol consumption by the subject. Note that although no significant difference in the overall degree of advanced glycation of hemoglobin could be detected between non-diabetic rats offered a high-ethanol diet versus a no-ethanol diet, specific differences in the composition of glycation products and/or intermediates may occur between these non-diabetic groups.

Although the data obtained in diabetic animals confirm, in an in vivo situation, the inhibitory effect of ethanol on AGE formation, only a small and not statistically significant effect was observed in the alcohol versus non-alcohol treated non-diabetic rats. In general, non-diabetic animals show a much lower level of protein glycation, as measured by currently available assays. More pronounced decreases in AGEs may be observed with longer-term ethanol administration and/or by studying protein and tissue components that have a longer life in vivo than red cell hemoglobin.

Specific Amadori-acetaldehyde adducts (AAAs) may occur on proteins or other biomolecules in ethanol-fed subjects, for instance, which AAAs could be identified by specific chemical or immunological characteristics.

TABLE I

| | Blood Glucose | Diet | Hb-AGE (mean ± sd) |
|---|---|---|---|
| Group 1 | diabetic | control | 3.1 ± 0.7 |
| Group 2 | diabetic | ethanol | 1.5 ± 0.6 |
| Group 3 | normal | control | 1.5 ± 0.5 |
| Group 4 | normal | ethanol | 1.6 ± 0.4 |

EXAMPLE 4

Figure 7A:
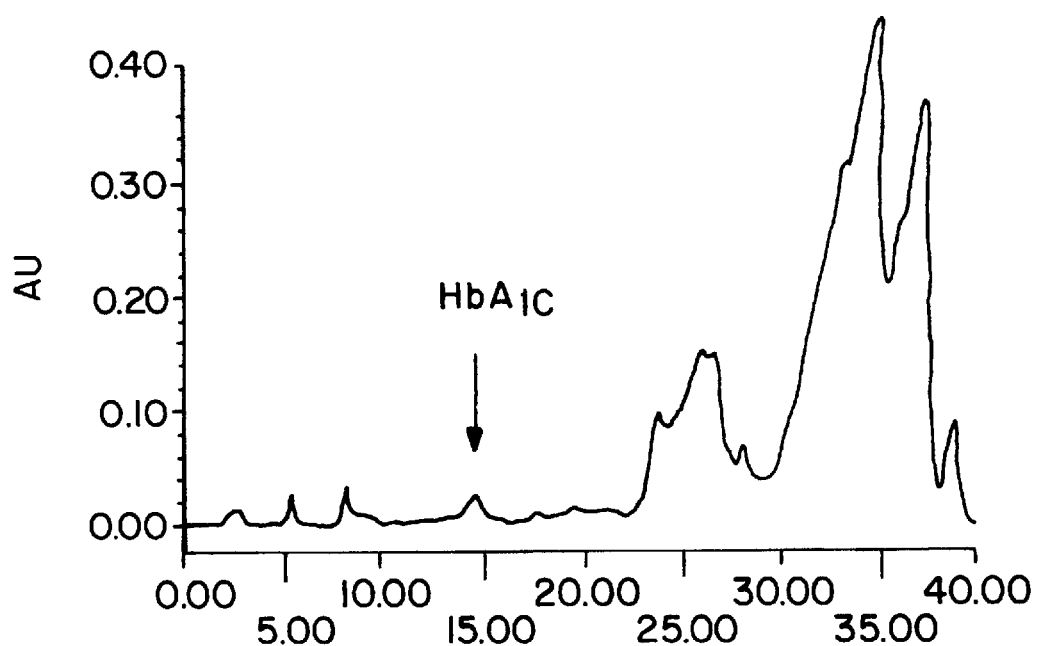
FIG. 7 are plots of HPLC (ion exchange chromotography) profiles of the hemolysates obtained from four groups of rats displayed in panels (a–d).
Figure 7B:
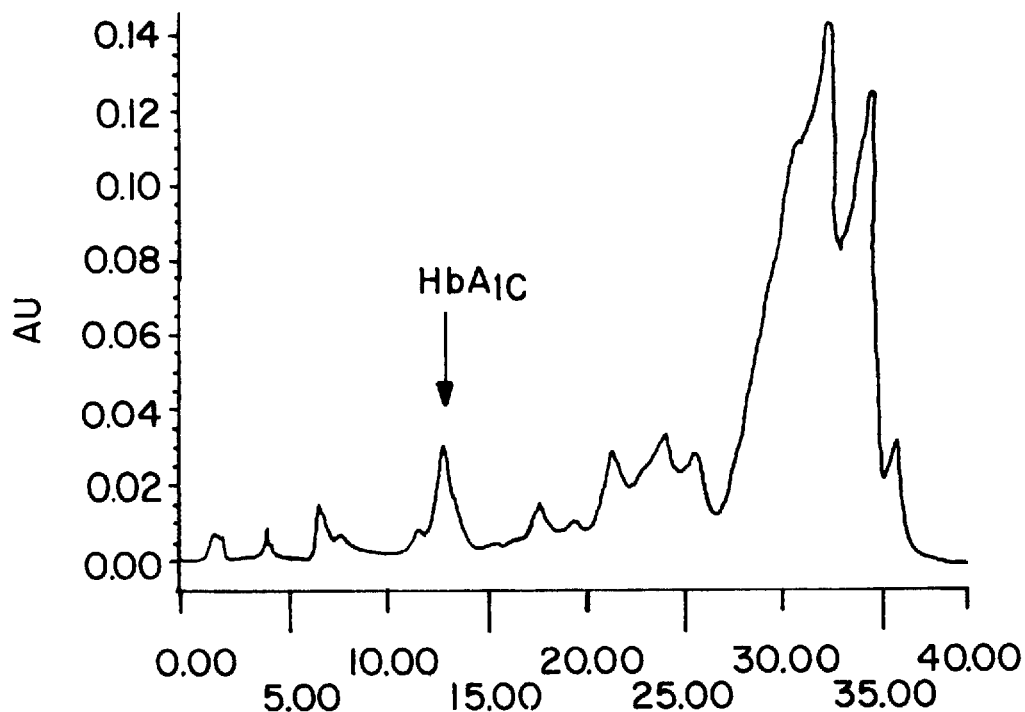
Figure 8A:
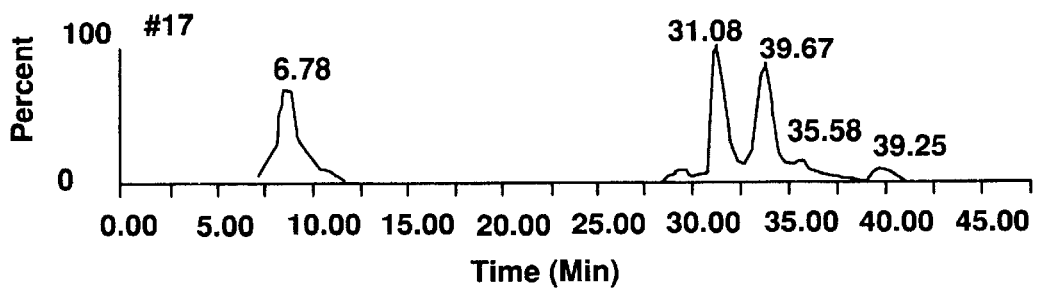
FIG. 8 shows the plots of a reverse phase liquid chromatography connected to an electrospray ionization mass spectrometer (LC-MS) of fractions containing $Hb_0$ and $HbA_{1c}$-acetadehyde adduct from the hemolysate of alcohol-treated diabetic rats.
Figure 8B:
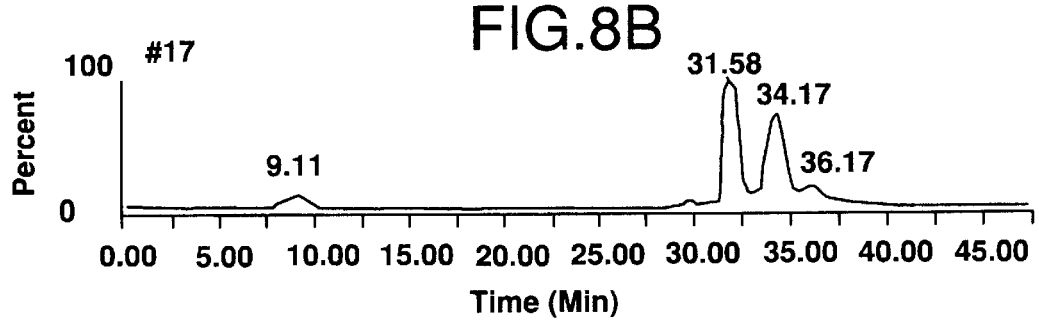
Figure 8C:
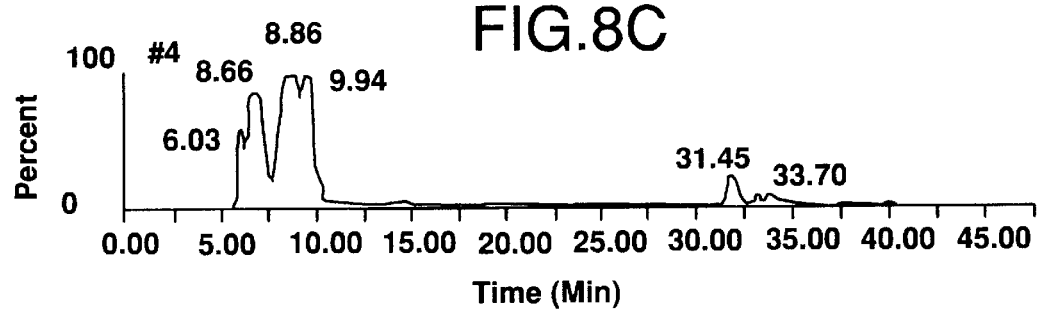
Figure 8D:
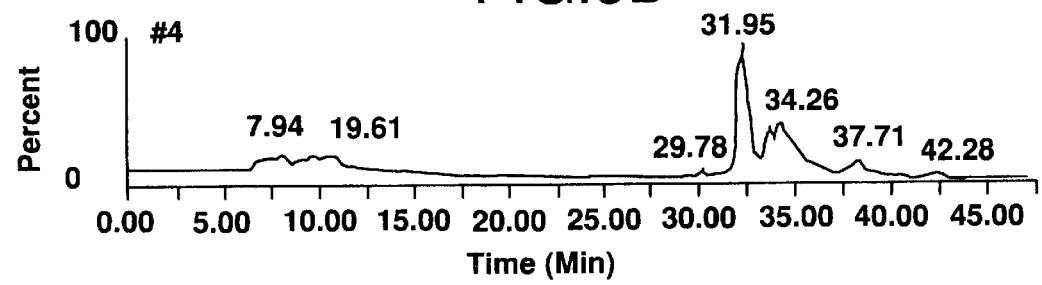

In an attempt to identify chemically the hemoglobin $A_{1c}$-acetaldehyde adduct ($HbA_{1c}$-AA) from alcohol-fed diabetic rats, a HPLC-based method was developed to study changes to hemoglobin induced by acetaldehyde in vivo. The hemolysates were obtained after standard workup of the red blood cells and analyzed by a Poly CAT A cation-exchange column in stepwise salt and Ph gradient. The mobile phases used were solution A: 40 mM Bis-Tris, 4 mM KCN, and 5 mM EDTA (pH 6.8), and solution B consisting of solution A and 0.2M NaCl (pH 6.8). The gradient program consisted of initial conditions of 78% A and 22% B, increasing to 56% B at 16 minutes, and 100% B at 22 minutes, and back to 22% B at 35 minutes. The flow rate was held constant at 1.0 ml/minute and the effluent absorbency was monitored at λ415 nm. The HPLC profiles of the hemolysates obtained from four group of rats are displayed in panels (a–d) of FIG. 7. This method distinguished 23 hemoglobin fractions. In a comparison between the hemolysate profile of non-diabetic and diabetic, a clear difference in the $HbA_{1c}$ concentration as well as in the shape and integration of the area eluted between 18 and 23 minutes (FIG. 7, panels a and b). Of note, in Panel c, the HPLC profile of diabetic rats which had consumed alcohol is similar to that of non-diabetics. In the 18–23 minute elution range, the hemoglobin-HPLC profile of diabetic rats was restored to the shape of non-diabetics (compare panels b and c) by alcohol consumption, which could be due to the fixation of $HbA_{1c}$ by acetaldehyde.

An analysis of the globin chains from certain hemoglobin fractions from the diabetic, ethanol diet group (above) was carried out using a reverse phase liquid chromatography coupled to electrospray ionization mass spectrometry (LC-MS) as shown in FIG. 8. The α- and β-chains of the native, unaltered fraction ($Hb_0$) were eluted at about 31 and 34 minutes, respectively (FIG. 8). The assignment of the chains was based on the molecular weight as indicated by mass spectra of α-chain (15198 Daltons) and β-chain (15861 Daltons). To determine the accuracy of this procedure, $HbA_{1c}$ was also analyzed, and the results are shown in FIG. 8.

The α- and β-chains eluted under similar conditions at about 31 and 34 minutes, respectively, and the mass spectra displayed a molecular ions of m/z 15199 (α-chain) and 16011 (β-chain). As expected, the β-chain displayed an increase of 162 Daltons compared to the parent β-chain obtained from Hbo due to the glycation of the N-terminal. Applicants next identified and characterized molecular species from a fraction containing an $HbA_{1c}$-acetaldehyde adduct similar to our in vitro model. We expected this adduct to elute faster from the poly CAT A column because the order of elution from cationic exchangers correlates with isoelectric points. Therefor several faster running fractions were analyzed by LC-MS. As expected, the LC-MS profile of one of these fractions showed a peak at about 31.9 minutes, indicating the presence of unmodified α-chain, as well as three other peaks which were related to β-chain based on their elution time (approximately 33.5, 34.2 and 37.7 minutes). ESMS spectra of two of these peaks displayed a molecular ion of 16070 and 16317 Daltons and remain to be further characterized. Interestingly enough, of note, the ESMS spectrum of the third peak gave a molecular weight of 16040.0 Daltons (FIG. 9A) which is consistent with the mass of the β-chain of the $HbA_{1c}$+acetaldehyde-$H_2O$.

These studies demonstrate an efficient way to stabilize the early states of advanced glycation by fixation of the cyclic form of the AP in vitro. Upon stabilization of the AP with acetaldehyde, its progress towards AGEs formation has been inhibited dramatically as indicated by AGE-ELISA (monoclonal and polyclonal antibodies) and fluorescence spectroscopy. Furthermore, the structure of AAA was characterized by mass spectroscopy and $^1$HNMR. In a second model system in vitro, bovine serum albumin was used as the target for advanced glycation and the inhibition of AGEs after in vitro glycation and further treatment with acetaldehyde was studied. After establishing the in vitro models, AGEs formation in a group of diabetic and non-diabetic rats fed either a control or an ethanol-supplemented diet was studied. The AGEs levels in diabetic rats fed an ethanol diet were reduced to the range of AGEs in normal rats. Interestingly, the HPLC profile cation exchange chromatography profile of the red-cell hemolysate from diabetic rats on an ethanol-supplemented diet is similar to that of normal rats. Ethanol is converted into acetaldehyde by alcohol dehydrogenase. The dramatic decrease in the level of AGEs in diabetic rats on an ethanol-supplemented diet may be ascribed to the action of acetaldehyde on Amadori and Heyns rearrangement products. As shown, acetaldehyde can target $HbA_{1c}$ and form a stable AAA-type compound.

Globin chains from the diabetic, ethanol-supplemented diet group were separated by reversed phase HPLC and analyzed by electrospray mass spectrometry. $Hb-A_{1c}$-acetaldehyde adduct was isolated in a fraction which eluted faster than $Hb-A_{1c}$ in the cation exchange chromatography and the β-chain showed an apppropiate molecular weight increase due to the attachment of acetaldehyde to the early glycation product, $HbA_{1c}$.

EXAMPLE 5

A variety of aldehydes are expected to be active in inhibiting the undesired browning of proteins and other biomolecules, either in vitro or in vivo or both. Assays are provided for the discovery of such activity, so that potentially useful inhibitors of browning may be discovered. A sample of soluble protein (BSA, for instance), which is known to be subject to advanced glycation, may be incubated in the presence of glucose or another reducing sugar, in aqueous buffer at neutral pH, for example, such that the protein will accumulate modifications by advanced glycation. If various aldehyde test agents then are separately included in parallel incubations, those aldehydes that are active in inhibiting the Maillard reaction may conveniently be identified by the lower amount of AGEs that accumulate on the sample protein in the presence of a test aldehyde compared to the number of AGEs that accumulate in the absence of such an aldehyde agent. For convenience, AGEs may be identified by any of several methods well known in the art, e.g., visual inspection for colored products, tests for protein crosslinking, fluorescence spectrophotometric tests for characteristic absorbance/emission maxima, AGE receptor-based assays, and AGE-specific immunoassays including, for instance, AGE-specific ELISAs based on anti-AGE antibodies. Optionally, the test incubations may be sealed, and the temperature of the incubation artificially elevated (as by a constant temperature bath) to accelerate the Maillard processes so that browned products accumulate more quickly. The addition of chelating agents and antioxidants may optionally be included so as to reduce the number of confounding metal-catalyzed and oxidizing reactions in the incubation mixture. Dose/response protocols, in which the aldehyde test agents are present in various doses are useful to identify potential inhibitors of advanced glycation of different potencies; those aldehydes which are active at lower concentrations would constitute a preferred group to further examine for additionally desirable characteristics, depending on the specific contemplated use. In accordance with this assay method, for instance, the various GRAS (i.e., Generally Recognized As Safe and so listed by the U.S. FDA) aldehydes can be tested for efficacy in inhibiting advanced glycation. Particularly effective GRAS compounds could then be further tested for compatibility as agents useful as Maillard inhibitors in vivo (e.g., to prevent protein aging or diabetic complications) or in vitro (e.g., to prevent food spoilage, the development of unpalatability, or inactivation of chemical or pharmaceutical compounds caused by non-enzymatic glycation and crosslinking during prolonged storage). Presently used food preservatives and discoloration preventives such as sulfur dioxide, known to cause toxicity including allergy and asthma in animals, might be replaced with compounds such as those described herein; such alternative inhibitors of Maillard reactions in foodstuffs and other comestibles are highly desirable. Agents of the present invention are of utility in this regard, as well as in pharmaceutical compositions to inhibit advanced glycation in vivo. Use in vivo is particularly indicated in aging and diabetes when the accumulation of AGEs in the body causes a number of pathogenic processes, both directly due to the chemical reactivity of AGEs and indirectly due to the interaction of AGEs with specialized cellular receptor systems, which interaction triggers a wide variety of normal and pathophysiological cellular responses.

EXAMPLE 6

Acetaldehyde-Amadori adduct (AAA) and related compounds of the present invention also find utility as antigens or haptens, to elicit antibodies specifically directed to AAA and AAA-like structures. Such antibodies, likewise of the present invention, are useful in turn to identify AAA structures of the present invention. By constructing immunoassays employing anti-AAA antibodies of the present invention, for instance, the degree to which proteins are modified by AAAs can be measured. As discussed above, and depending on the half-life of the protein so modified, immunochemical measurement of AAA epitopes on a protein sample, such as hemoglobin, provides an index of recent alcohol (ethanol) consumption. Likewise, immunochemical detection of AAA epitopes on circulating and/or tissue proteins can be used to monitor the course of therapy with agents of the present invention, which aldehyde-based agents are directed toward inhibition of advanced glycation by locking spontaneously formed Amadori products in their closed, and hence unreactive, conformation.

AAA-modified BSA for use as an immunogen can be prepared according to the following reaction Scheme III below.

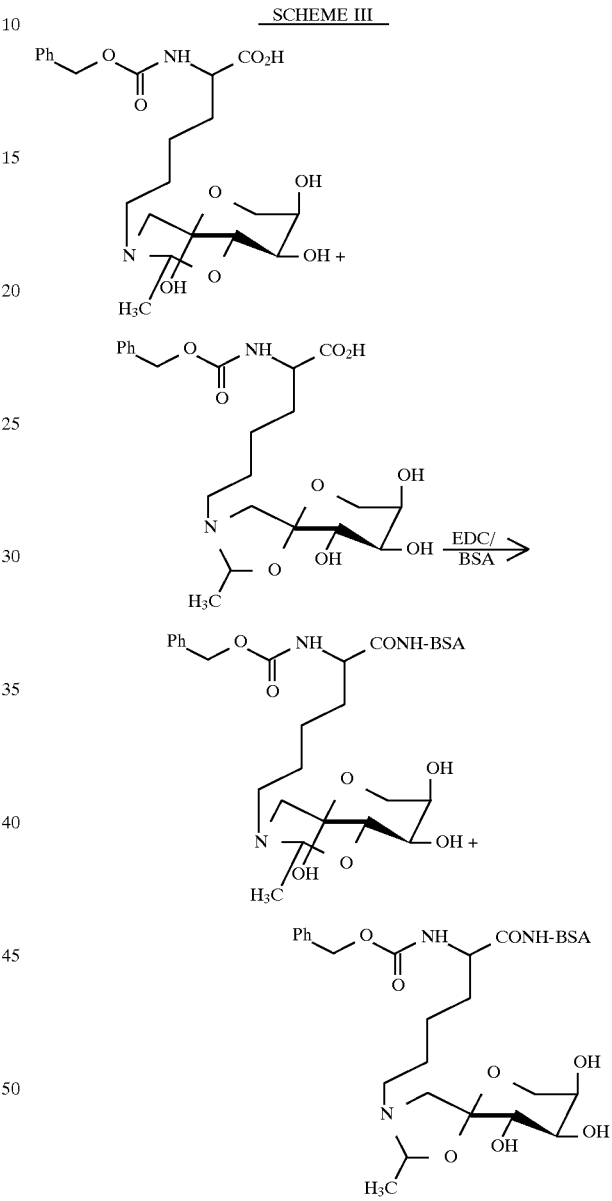

AAA may also be synthesized ab initio by the following procedure shown in Scheme IV below.

SCHEME IV

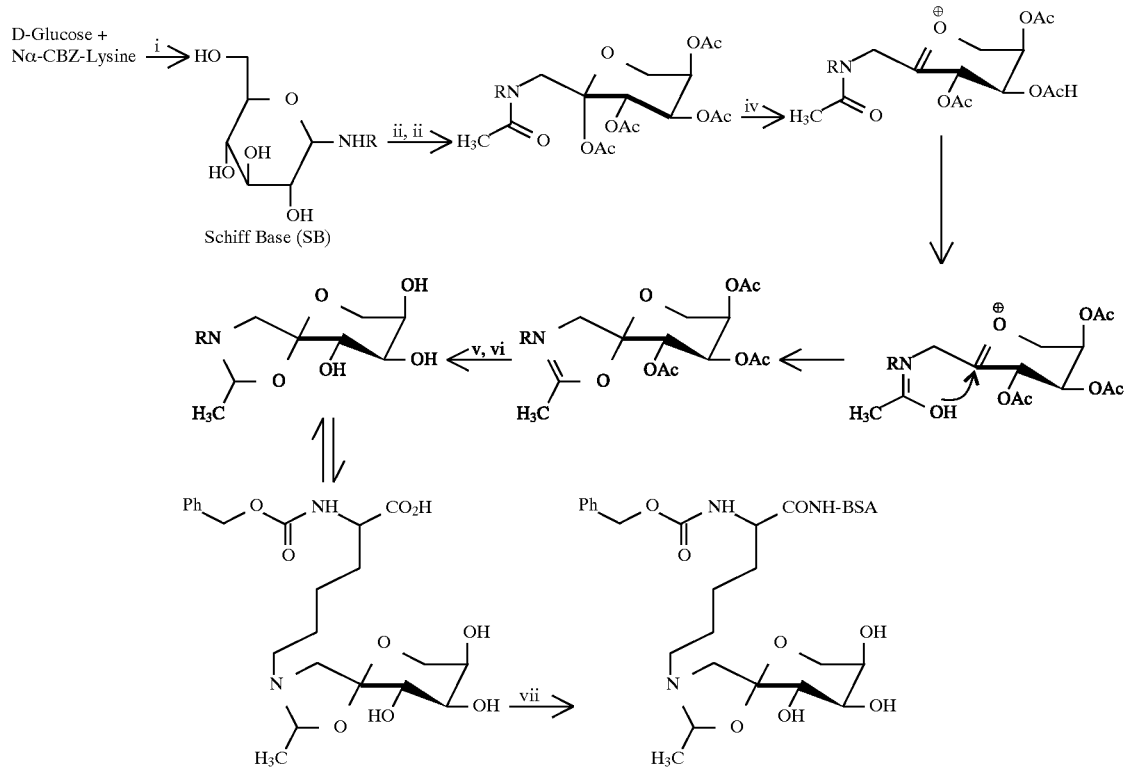

In this reaction sequence, the desired AAA of formula VII is prepared by acetylation of the synthetic Amadori product, CBZ-lysine-AP, shown in Scheme II, with acetic anhydride in the presence of pyridine to afford the pentaacetylated compound. Treatment of this compound with trifluoroacetic acid in dichloromethane affords the bicyclic system. Deacetylation of the tetracetylated bicyclic compound, followed by NaBH$_4$ reduction of the intact double bond within the five-membered ring yields the desired product.

Various haptens, antigens, and conjugated immunogens corresponding to the aldehyde-modified Amadori products of the present invention, including without limitation the acetaldehyde-modified CBZ-lysine-Amadori product described in Example 1, can conveniently be prepared, either by isolation from incubation mixtures or by direct synthetic approaches. CBZ-lysine-AP, for example, can be incubated with acetaldehyde in vitro and isolated, essentially as described in Example 1 (above). This AAA may then be used as an immunogen to raise a variety of antibodies which recognize specific eptitopes or molecular features thereof. In a preferred embodiment, AAA itself is considered a hapten, which is correspondingly coupled to any of several preferred carrier proteins, including for instance keyhole limpet hemocyanin (KLH), thyroglobulin, and most preferred, bovine serium albumin (BSA), using any of a number of well-known divalent coupling reagents such as a carbodiimide like EDC, according to protocols widely circulated in the art. Alternatively, the desired aldehyde-reacted Amadori product can be synthesized ab initio, essentially as described in Scheme IV for the Amadori-acetaldehyde adduct (AAA). Irrespective of the source, the AAA or other aldehyde-reacted Amadori product (or Heyns product), whether alone or coupled to a carrier protein, may be employed in any well-recognized immunization protocol to generate antibodies and related immunological reagents that are useful in a number of applications owing to the specificity of the antibodies for molecular features of the aldehyde-reacted Amadori product.

Following a preferred protocol, any of several animal species may be immunized to produce polyclonal antisera directed against the AAA-carrier protein conjugate, including for instance mice, rats, hamsters, goats, rabbits, and chickens. The first of three of the aforesaid animal species are particularly desired choices for the subsequent production of hybridomas secreting hapten-specific monoclonal antibodies. The production of said hybridomas from spleen cells of immunized animals may convenientally be accomplished by any of several protocols popularly practiced in the art, and which describe conditions suitable for immortalization of immunized spleen cells by fusion with an appropriate cell line, e.g. a myeloma cell line. Said protocols for producing hybridomas also provide methods for selecting and cloning immune splenocyte/myeloma cell hybridomas and for identifying hybridomas clones that stably secrete antibodies directed against the desired eptiope(s). Animal species such as rabbit and goat are more commonly employed for the generation of polyclonal antisera, but regardless of whether polyclonal antisera or monoclonal antibodies are desired ultimately, the hapten-modified carrier protein typically is initally administered in conjunction with an adjuvant such as Complete Freund's Adjuvant. Immunizations may be administered by any of several routes, typically intraperitoneal, intramuscular or intradermal; certain routes are preferrred in the art according to the species to be immunized and the type of antibody ultimately to be produced. Subsequently, booster immunizations are generally administered in conjunction with an adjuvant such as alum or Incomplete Freund's Adjuvant. Booster immunizations are administered at intervals after the inital immunization; generally one month is a suitable interval, with blood samples taken between one and two weeks after each booster immunization. Alternatively, a variety of so-called hyperimmunication schedules, which generally feature booster immunizations spaced closer together in time, are sometimes employed in an effort to produce anti-hapten antibodies preferentially over anti-carrier protein antibodies.

The antibody titers in post-boost blood samples can be compared for hapten-specific immune titer in any of several convenient formats including, for instance, Ouchterlony diffusion gels and direct ELISA protocols. In a typical direct ELISA, a defined antigen is immobilized onto the assay well surface, typically in a 96-well or microtiter plate format, followed by a series of incubations separated by rinses of the assay well surface to remove unbound binding partners. By way of non-limiting example, the wells of an assay plate may receive a dilute, buffered aqueous solution of the hapten/carrier conjugate, preferably wherein the carrier protein differs from that used to immunize the antibody-producing animal to be tested; e.g. serum from AAA/KLH conjugate-immunized animal might be tested against assays wells decorated with immobilized AAA/BSA conjugate. Alternatively, the assay surface may be decorated by incubation with the hapten alone. Generally, the surface of the assay wells is then exposed to a solution of an irrelevant protein, such as casein, to block unoccupied sites on the plastic surfaces. After rinsing with a neutral buffered solution that typically contains salts and a detergent to minimize non-specific interactions, the well is then contacted with one of a serial dilution of the serum prepared from the blood sample of interest (the primary antiserum). After rinsing again, the extent of test antibodies immobilized onto the assay wells by interaction with the desired hapten or hapten/carrier conjugate can be estimated by incubation with a commercially available enzyme-antibody conjugate, wherein the antibody portion of this secondary conjugate is directed against the species used to produce the primary antiserum; e.g. if the primary antiserum was raised in rabbits, a commercial preparation of anti-rabbit antibodies raised in goat and conjugated to one of several enzymes, such as horseradish peroxidase, can be used as the secondary antibody. Following procedures specified by the manufacturer, the amount of this secondary antibody can then be estimated quantitativley by the activity of the assoicated conjugate enzyme in a calorimetric assay. Many related ELISA or radioimmunometric protocols, such as competitive ELISAs or sandwich ELISAs, all of which are well-known in the art, may optionally be substituted, to identify the desired antisera of high titer; that is, the particular antisera which give a true positive result at high dilution (e.g. greater than 1/1000 and more preferably greater than 1/10,000).

Similar immunometric protocols can be used to estimate the titer of antibodies in culture supernatants from hybridomas prepared from spleen cells of immunized animals. In so characterizing antisera or hybridoma supernatants, it is desirable to employ a variety of control incubations. e.g. with different carrier proteins, related but structually distinct haptens or antigens, and omitting various reagents in the immunometric procedure in order to minimize non-specific signals in the assay and to identify reliable determinations of antibody specificity and titer from false positive and false negative results. The types of control incubations to use in this regard are well known. Also, the same general immunometric protocols subsequently may be employed with the antisera identified by the above procedures to be of high titer and to be directed against specific structural determinants in the aldehyde-modified Amadori products on biological samples, foodstuffs or other comestibles, or other amine-bearing substances and biomolecules of interest. Such latter applications of the desired anti-aldehyde-modified Amadori product antibodies, whether polyclonal or monoclonal, together with instructions and optionally with other useful reagents and diluents, including, without limitation, a set of molecular standards of the aldehyde-modified Amadori product, may be provided in kit form for the convience of the operator.

What is claimed is:

1. A compound of the formula VI or VIII

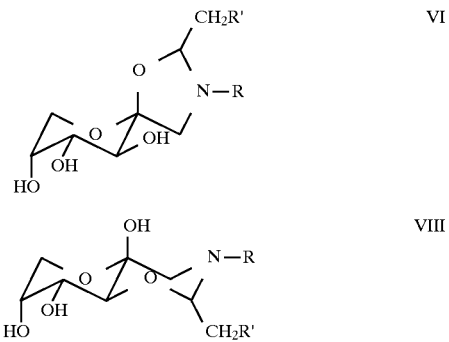

wherein R is the residue of an amino-containing amino acid, peptide, protein, biomolecule or compound, said compound of the formula VI or VIII prepared by reaction of the glycosyl-amino moiety of the early glycosylation product (also known as the Amadori product or the Heyns product) formed by the reaction of glucose, or other reactive sugars, with said amino-containing amino acid, peptide, protein, biomolecule, or compound with an agent containing a reactive aldehyde group; and $CH_2R'$ the residue of the reactive aldehyde group wherein R' is an alkyl group of 1–12 carbons, an alkenyl group of 1–20 carbon atoms containing 1–4 degrees of unsaturation, and alkynyl group of 1–20 carbon atoms containing one or more triple bonds, an aryl or a heteroaryl group, each of which can optionally be substituted by one or more halogen or hydroxyl groups.

2. The compound according to claim 1, wherein said agent containing a reactive aldehyde group is acetaldehyde, or an agent which is converted metabolically in vivo to acetaldehyde.

3. The compound according to claim 1, which is 1-deoxy-1-alkylamino-1,2-N,O-ethylidene-β-D-fructopyranose.

4. The compound according to claim 1, which is 1-deoxy-1-alkylamino-1,3-N, O-ethylidene-β-D-fructopyranose.

* * * * *

UNITED STATES PATENT AND TRADEMARK OFFICE
CERTIFICATE OF CORRECTION

PATENT NO. : 5,770,571                                          Page 1 of 2
DATED      : January 23, 1998
INVENTOR(S) : Anthony Cerami et al.

It is certified that error appears in the above-identified patent and that said Letters Patent is hereby corrected as shown below:

Please correct Claim 1 by replacing two structures in column 30, lines 20-34 with:

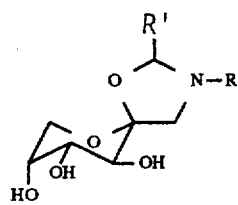

VI

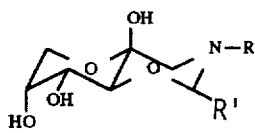

VIII

UNITED STATES PATENT AND TRADEMARK OFFICE
CERTIFICATE OF CORRECTION

PATENT NO. : 5,770,571
DATED : January 23, 1998
INVENTOR(S) : Anthony Cerami et al.

It is certified that error appears in the above-identified patent and that said Letters Patent is hereby corrected as shown below:

and
in column 30, line 45, please change "CH2R'" to --R'--.

Signed and Sealed this

Twentieth Day of June, 2000

Attest:

Q. TODD DICKINSON

*Attesting Officer*  *Director of Patents and Trademarks*